(12) United States Patent
Hahn

(10) Patent No.: US 6,394,802 B1
(45) Date of Patent: May 28, 2002

(54) DEVICE FOR PRODUCING TOOTH IMPRESSIONS AND IMPRESSION TRAY THEREFOR

(76) Inventor: Rainer Hahn, Schwabstr. 11, 72074 Tübingen (DE)

( * ) Notice: Subject to any disclaimer, the term of this patent is extended or adjusted under 35 U.S.C. 154(b) by 0 days.

(21) Appl. No.: 09/142,484

(22) PCT Filed: Mar. 5, 1997

(86) PCT No.: PCT/EP97/01110

§ 371 (c)(1),
(2), (4) Date: Feb. 23, 2000

(87) PCT Pub. No.: WO97/32536

PCT Pub. Date: Sep. 12, 1997

(30) Foreign Application Priority Data

Mar. 6, 1996 (DE) .......................... 196 08 546
Jul. 9, 1996 (DE) .......................... 196 27 517

(51) Int. Cl.⁷ ................................ A61Z 9/00
(52) U.S. Cl. ........................................... 433/37
(58) Field of Search ................ 433/37, 199.1, 433/213, 214

(56) References Cited

U.S. PATENT DOCUMENTS

| 1,437,844 A | * | 12/1922 | Henderson | |
|---|---|---|---|---|
| 2,311,158 A | * | 2/1943 | Conway et al. | 433/214 |
| 3,768,164 A | * | 10/1973 | Breads | 433/213 |
| 5,316,473 A | * | 5/1994 | Hare | 433/37 |
| 5,370,533 A | * | 12/1994 | Bushell | 433/37 |
| 5,551,872 A | * | 9/1996 | Mena | 433/37 |
| 5,667,386 A | * | 9/1997 | Black et al. | 433/213 |

FOREIGN PATENT DOCUMENTS

| DE | 1491212 | * | 4/1969 | 433/214 |
|---|---|---|---|---|
| DE | 2734030 | * | 2/1979 | 433/214 |
| DE | 4116190 | * | 11/1992 | 433/214 |
| DE | 4130701 A | * | 4/1993 | |
| DE | 9313561 U | * | 12/1993 | |
| EP | 519195 A | * | 12/1992 | |

* cited by examiner

Primary Examiner—Todd E. Manahan

(57) ABSTRACT

A tray for producing impressions of dental arches includes a peripheral edge wall that forms a sealing point with soft tissue in the patient's mouth. The interior of the tray is connected via a plurality of vacuum connection pieces to a suction arrangement. Disposed in an impression space provided by the tray is an impression material distributor tube that conveys impression material, preferably to the rear impression space. The distributor tube is connected to an impression material source.

90 Claims, 27 Drawing Sheets

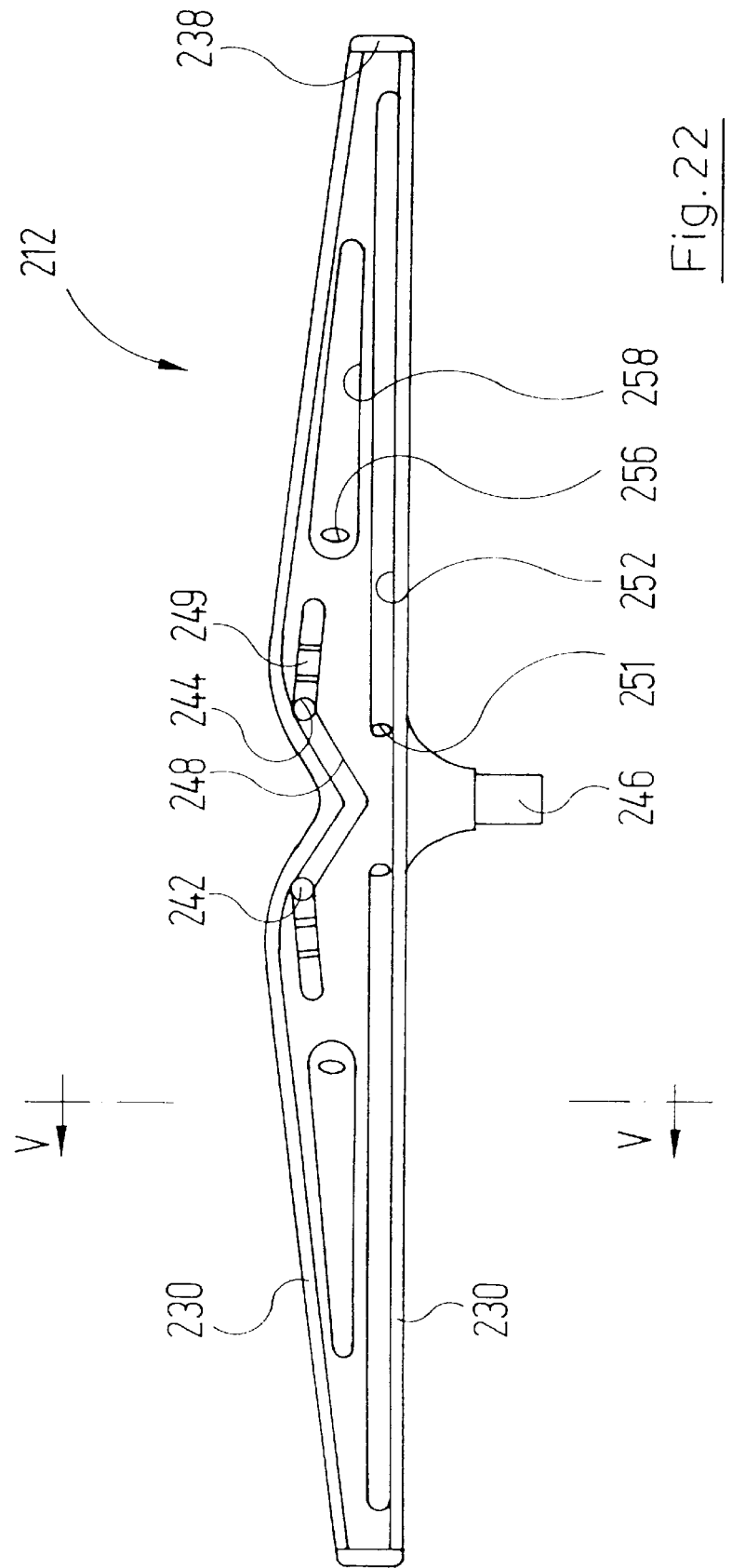

DEVICE FOR PRODUCING TOOTH IMPRESSIONS AND IMPRESSION TRAY THEREFOR

BACKGROUND OF THE INVENTION

The present invention relates to a device for producing tooth impressions with a tray that can cover a plurality of adjacent tooth positions of a jaw, the contour of the tray roughly matching the contour of the jaw.

Such a device is described in DE 41 30 701 A1.

In practice no completely satisfactory tooth impressions are obtained with such a known device.

SUMMARY OF THE INVENTION

The present invention is therefore intended to provide an improved device for producing tooth impressions with a tray that can cover a plurality of adjacent tooth positions of a jaw, the contour of the tray roughly matching the contour of the jaw, so that extremely accurate impressions can be obtained.

This objective is achieved according to the invention by a device that has the following features: The free edges of the tray walls run so that they can form together with soft tissues of a patient's mouth a sealing point, which tray is provided with at least one impression material connection element communicating with the interior of the tray, and with a source for liquid hardenable impression material that is connected to the impression material connection element, wherein the tray has at least one vacuum connection element communicating with the interior of the tray and that is connected to a reduced pressure source.

The following functions and advantages are achieved with a device according to the invention for producing tooth impressions:

The tray can be accurately positioned and firmly secured when used either on the upper jaw or on the lower jaw, and more specifically independently of mucous membrane activity or tongue movements. The tray does not need to be held by the dentist or by a dental assistant. Accordingly, not only are handling and manipulation substantially simplified, but the production of an impression is also less uncomfortable for the patient.

The tray is tightly sealed at the edge, so that no liquid impression material can escape from the tray and reach, for example, the throat.

On account of the fact that the impression space, which is bounded on the one hand by the tray and on the other hand by the patient's teeth and the gums surrounding the teeth, is according to the invention subjected to a reduced (sub-atmospheric) pressure, the edges of the gums are retracted slightly from the neck of the teeth, so that the initially liquid impression material also forms a good impression of the region of the teeth lying adjacent to the edge of the gums.

The device according to the invention employs the closed impression space already referred to above. This space may, before being filled with an impression material or also in application situations not connected with making impressions, also be used for the selective application of therapeutic agents, especially in the form of liquids, aerosols or gases. Such agents may for example include haemostatics, wetting agents, astringents disinfectants, fluoride solutions, desensitizing substances, deodorants, flavouring agents, substances for periodontal treatment, substances for caries prophylaxis, substances preventing plaque formation, wetting agents such as sodium lauryl sulphate, anitadhesives in the form of liquid solutions or aerosols, for example Delmopinol or Triclosan solutions, agents for dealing with salivary gland secretions, or physical therapeutic agents such as water, warm air and the like.

The device according to the invention involves a directed flow of liquids, for example of the aforementioned therapeutic agents or of the impression compound, from the impression material connection element via a predetermined flow pathway to the vacuum connection element. These added liquids flush out any liquids such as saliva and blood that may be present on the aforedescribed flow pathway. In this way a complete filling of the impression space is ensured. The relative movement between the liquids and the longitudinal axes of the teeth takes place at an angle other than zero, preferably at an angle of 90°. In this way preferred flow directions can be established, from distal to mesial or vice versa, or from buccal to oral or vice versa. With the conventional impression techniques the tray filled with the impression material is mounted on the jaw in a direction perpendicular to the plane of the jaw, which means that the relative movement between the impression material and the teeth occurs parallel to the longitudinal axis of the teeth.

When using the device according to the invention the production of the tooth impression can also be combined with a therapeutic effect by for example adding a therapeutic agent to the impression material itself.

Also, various steps in the production of the impression can be combined, for example by adding, the wetting agent to the impression material itself instead of applying the wetting agent in a preparatory step to the surfaces of which an impression is to be made, or in the preparation of the material, thereby avoiding the need for this preparatory step.

The liquid hardenable impression materials that are used in the device according to the invention have a relatively high viscosity compared to water, typically that of the so-called "thin-bodied" impression or correcting compounds that are used for intraoral impression work (in contrast to kneadable impression compounds). For this reason they arc added under a positive pressure to the impression material connection element, and the reduced pressure generated in the impression space is chosen so that, on the one hand, the desired good edge sealing of the tray and the desired good positioning of the tray is ensured, but on the other hand no haematomas are formed in the tissues cooperating with the edges of the tray and the patient is not subjected to severe discomfort or pain.

The applied reduced pressure and the feed pressure for the impression material as well as the filling amount per unit time and the viscosity of the impression compound are matched to one another. While the impression space is being filled the reduced pressure and the feed pressure are maintained substantially constant, so that the impression material fills the impression space at a uniform rate (and thus in particular without any interruption), the front of the impression material displacing forwardly any liquids (water, saliva, blood) present in the impression space. These liquids are then sucked out through the vacuum connection element. This continuous filling of the impression space ensures that no enclosed bubbles on "shadow" regions formed by teeth against the filling direction are obtained in the impression.

Alternatively, during the continuous filling of the impression space the reduced pressure may first of all be lowered and then raised somewhat towards the end of the filling procedure, the reduced pressure and/or the conveying pressure being controlled overall in such a way as to ensure a continuous flow of the impression material. Care is preferably taken to ensure that the impression material does not come to a stop within the tray.

The filling of the impression space under a vacuum, which in the device according to the invention preferably takes place perpendicularly to the longitudinal axis of the teeth, ensures in particular that full impressions can be made without any delay also of undercuts lying underneath the tooth equator and of gaps between the teeth. Also, impressions of the tooth surfaces are made in a largely pressure-free manner, thereby avoiding errors due to elastic reverse movement of the impression material or due to any eddy formations on sharp tooth edges, for example in the region of preparation edges.

Tooth impressions using the device according to the invention are produced with a high certainty of success, with savings in time, and in a way that is more pleasant for the patient. More precise tooth impressions are obtained than is the case with conventional techniques. This does not only mean that the impressions have smaller tolerances, but also that there is a better wetting of more surfaces, even of surfaces in difficultly accessible places.

As already mentioned above, in the use of the device according to the invention the movable marginal gingiva is retracted from the fixed adjacent tooth surfaces. In this way a good impression can be made directly of the region of the edge of the gum. This is particularly important when teeth are prepared for example to receive crowns. The preparation boundary frequently lies at the level of the edge of the gum (paramarginal) or even apically (in the direction of the root) of this region (subgingivally). For the purposes of complete coverage and for the necessary coverage of about 1 mm of the tooth root surface apically to the preparation boundary (essential for the correct contouring of the crown), when the device according to the invention is used the impression material is able to flow between the gum and tooth root surface.

This impression procedure is made possible by the previously described retraction of the edge of the gum under the acting vacuum, the already aforedescribed directed flow of the impression material also however being favourable since the liquid column (saliva or sulcus fluid) present in the gum sulcus or in gum pockets in the gap between the edge of the gum and tooth surface is displaced away from the impression material. Such a displacement does not occur with conventional impression techniques, since in these the teeth come into contact occlusally with the impression material, which means that the various sections of a gum edge of a tooth are coated more or less simultaneously with impression material. The liquid column lying between the edge of the gum and the tooth surface is thus enclosed, and since it cannot be compressed a corresponding bubble-like void is obtained in the finished impression, or the production or impressions of subgingivally lying tooth surfaces or prepared tooth surfaces is prevented.

It is understood that these tooth surfaces localised in the region of the marginal edge of the gum can, after drying in a current of air, also first of all be sprayed all over with a thin-bodied impression material before the tray according to the invention is inserted into the patient's mouth. Following this first spraying the tray according to the invention is then mounted in position, a vacuum is applied, and the tray is filled with impression material. The impression material is chosen so that it is compatible with the initially applied thin-bodied impression material and combines with the latter during the course of the hardening. The impression material that was first of all sprayed on manually also serves at the same time as a space occupier that prevents refilling of deep pockets with liquids such as sulcus fluid or blood from the base of the pocket after it has previously been dried. In the aforedescribed procedure some of the material injected beforehand is displaced, while other parts mix thoroughly with the impression material introduced subsequently during the use of the tray according to the invention. Any bleeding that has occurred in the meantime is again displaced before the front of the impression material introduced into the tray and is sucked off at one of the vacuum connection elements. This procedure has proved effective for example in the case of patients with deep gum pockets and subgingival preparations.

It has proved particularly effective, before making the impression, to insert a retracting thread into the gum sulci preferably of the prepared or to be prepared teeth and to leave this in situ until after the impression has been made, whereby the production of impressions of paragingival or subgingival prepared teeth surfaces is furthermore simplified and made more precise using the method according to the invention.

Furthermore, the inflow of blood into the impression tray that is under a vacuum can be successfully avoided in this way, especially in the case of inflamed gingiva (gums), which have an increased tendency to bleed.

The retraction thread may be impregnated with therapeutically active substances, for example to stop bleeding.

In the case of teeth to be prepared having a preparation boundary to be paragingivally or subgingivally extended and exhibiting somewhat deeper gum pockets, it has proved particularly effective to insert one or more retraction threads above one another into the gum pockets before starting the preparatory work, in order thereby to prevent damage to the marginal gum edge by the preparation instruments, at least the most apical retraction thread remaining in situ until after the impression has been produced.

The reduced pressure source establishes a pressure drop in the range between 10 and 500 mbar, preferably between 10 and 200 mbar, and particularly preferably between 50 and 150 mbar. If the vacuum generated in the impression space is chosen according to this feature, then on the one hand this ensures a reliable positioning of the tray in the patient's mouth, and on the other hand the forces exerted by the free edges of the tray on the soft tissue in the patient's mouth are not so large as to cause the patient pain. The particularly preferred values for the reduced pressure produced in the impression space ensure that the gum edges are retracted slightly from the teeth, so that a good impression of the teeth in the gum region can be produced.

The reduced pressure source has a suction arrangement and a reduced pressure regulator connected in front of its suction opening. The development of the invention according to this feature permits the reduced pressure produced in the impression space to be adjusted in each case according to the circumstances of each patient. In particular the reduced pressure can be adjusted by visually monitoring the gum edge using an at least partially transparent tray, so that the gum edge retracts just a little.

The suction arrangement has a venturi nozzle whose feed inlet is connected to a compressed air line. The development of the invention according to this feature permits a reduced pressure of desired magnitude to be produced in a simple manner using compressed air that is of course available in a dentist's surgery. The production, according to the venturi principle, of the reduced pressure required by the device according to the invention can also be employed in combination with an existing suction device in the surgery. Alternatively, the existing suction device in the surgery can also be used in conjunction with an additional reduced pressure regulator.

An impression material distributor tube extends in the longitudinal direction of a curved impression space predetermined by the tray, which tube has at least one opening, is preferably open at its ends, and preferably also has at least one outlet opening in the tube wall, open to the interior of the tray, an outlet opening pointing to the tooth position preferably additionally being provided for each tooth position. The development of the invention according to this feature enables a defined vacuum to be maintained in the impression space up to the end of the filling procedure.

The tray covers a whole tooth arch and has a symmetrical shape relative to a longitudinal centre plane, wherein the distributor is likewise symmetrical relative to the longitudinal centre plane of the tray and is extended by the two arms of the impression space having a U-shaped geometry in plain view. The development of the invention according to this feature is of advantage with regard to a rapid and uniform inflow of the impression material into the impression space.

The tray has a plurality of vacuum connection elements, which are preferably arranged symmetrically to its longitudinal centre plane. The same comments apply as regards the development of the invention according to this feature. By virtue of the fact that a plurality of vacuum connection elements (at least three) is arranged symmetrically relative to the centre plane, a complete filling of the impression space is ensured even in the case where the jaw relationships are asymmetric or where the patient has only a partial set of teeth. If towards the end of the filling procedure one or more of the vacuum connection elements is/are closed by impression material, then in addition a reduced pressure is produced and liquids displaced by the front of the impression material are suctioned off by the still free connection elements, so that the last phase too of the filling procedure takes place in a bubble-free manner.

At least some of the vacuum connection elements communicate with associated vacuum distributor lines, which extend over a plurality of teeth positions and have at least one suction opening, and preferably have a suction opening for each of the teeth positions. The development of the invention according to this feature is of advantage with regard to an even more uniform reduced pressure charging during the filling of the impression space and with regard to an even more uniform removal of liquids displaced in front of the impression material.

If a vacuum distributor line is used as proposed according to this invention, in conjunction with an impression material distributor line that is the subject matter of the invention, then flow directions of the impression material from buccal to oral or vice versa can be established, such flow patterns being able to be realised particularly effectively if aligned openings in the impression material distributor line and the vacuum distributor line are associated with each tooth position.

The vacuum connection elements are connected via a common reduced pressure line to the reduced pressure source. In a device according to this feature the various vacuum connection elements are likewise connected to a vacuum, which is also of advantage with regard to a rapid and uniform filling of the impression space. In practice the clear diameter of the vacuum connection elements is smaller than that of the common reduced pressure line. If impression material is drawn into a connection element because the tray is full at this point, only a part of this material is further aspirated, since on account of its high viscosity it can move only with difficulty in the narrow channel of the connection element. The corresponding vacuum connection clement is thus closed. The impression material cannot however flow into the common reduced pressure line, with the result that the other vacuum connection elements are in addition exposed to reduced pressure through this line. After closure of a vacuum connection element the flow pattern of the impression material is changed, more specifically by the fact that the impression material is added to the still unfilled sections of the impression space. The arrangement and number of the vacuum connection elements can be derived from a simplified model of the shape of the jaw, according to which the rows of side teeth up to the canine tooth are regarded as a straight line, and the front tooth region between the two canine teeth is regarded as a further straight line. The nodal points for the suction then lie in each case mesially with respect to the canine teeth between the canine tooth and the lateral incisor at the points of intersection of the straight lines, and in addition at least one nodal point is provided symmetrically between the two middle incisors.

The impression material connection elements and the vacuum connection elements are carried by a tray section formed as a disposable part, whereas the reusable remainder of the tray is formed as a sterilized part. The device according to this feature obviates the need for a costly cleaning of the connection elements. The reusable part of the tray may be manufactured from rigid or soft material. That part of the tray formed as a disposable part is preferably rigid and designed so that it is largely surrounded by the added impression material. This arrangement means that the tray assembled from the individual tray parts is overall stiff and torsionally rigid, while at the same time that part of the tray designed as a disposable part together with the hardened impression material forms a rigid part that can be sent to the dental laboratory, minus the reusable part of the tray. The use of a pliable reusable tray part is on the other hand advantageous having regard to a simple and inexpensive sealing between the tray parts. If desired, in addition only those sections of the tray segment designed as a disposable part, which lie adjacent to the gum, may be made of soft elastic material.

The impression material connection elements and the vacuum connection elements are carried by a central section of an external edge wall of the tray, the central section of the external edge wall, optionally in combination with the connection elements, preferably being formed as a handle. With a tray of the type disclosed in this feature, the various connection elements for impression material and the reduced pressure charging are arranged in a common front region of the tray, which simplifies the manufacture of the flow connections.

The impression material connection element is arranged in an apron of the external edge wall of the disposable tray part, which element engages in a complementary recess of the external edge wall of the reused tray part. According to this feature connection elements having a large flow cross-section may also be provided in a small front central region of the tray, these connection elements belonging to the part of the tray optionally designed as a disposable part.

The cooperating edges of the reused tray part and disposable tray part are sealed with respect to one another via a groove/tongue joint and/or a seal. According to this feature a good fluid seal is achieved between the reusable tray part and the disposable tray part. The impression space can therefore be subjected to a vacuum using a fairly weak suction arrangement. Alternatively or in addition, extra sealing compounds may also be provided at the points of contact between the tray segments, for example mouldable and/or hardening sealing compounds, for example silicone may be injected or plastic or plastically or elastically mouldable and hardening sealing compounds may be used, for example kneading compounds, silicones, waxes, plastics or the like. Furthermore, flexible tube-like sealing elements may be used at the points of contact between the tray parts.

The free edge of the tray carried an elastically flexible seal. The seal is carried by a bendable section of the disposable tray part. The seal is an expandable flexible hollow body that is connected to a compressed air source, or is an elastically deformable hollow body. The developments of the invention according to these features are advantageous having regard to an efficient, gentle sealing of the impression space involving the minimum of equipment.

The disposable tray part has at least one material longitudinal web running in the longitudinal direction of the impression space and a plurality of transverse webs running between the latter web and the external edge wall of the disposable tray part, the material longitudinal webs and the transverse webs being designed so that they permit a flow of the impression material in the longitudinal direction of the dental arch and/or a direction perpendicular thereto. If the disposable tray part is designed according to this feature then it can easily be handled as one unit, for example mounted on the reusable tray part, and moreover it still has a certain degree of flexibility in order that it can adapt to the shape of the reusable tray part so as to engage in a reliable frictional or snap-type manner with the latter. The weblike construction of the disposable tray part also saves material, which is particularly advantageous in the case of disposable tray parts.

The impression material distributor tube is connected to the tray edge part, and in particular is embedded wholly or partly therein. The development of the invention according to this feature ensures a precise positioning of the impression material distributor tube in the tray.

The tray is wholly or partly made of transparent material, in particular transparent plastics material, and in addition the vacuum connection elements are also preferably made of transparent material, in particular transparent plastics material. The development of the invention according to this feature enables on the one hand the correct mounting and positioning of the tray to be checked visually. Furthermore it can be checked visually whether the correct reduced pressure for the respective patient is set in the impression space (slight retraction of the gum edges). Finally, with a tray according to this feature the filling of the impression space with impression material can also be visually checked. The following features can furthermore be readily visually checked: the suction and removal of therapeutic agents or liquids such as blood or saliva from the impression space via the vacuum connection elements, as well as any blockage of the vacuum connection elements by aspirated impression material.

A section of the interior of the tray is separated by a sealing wall from the impression space, the free edge of the sealing wall being able to be placed tightly against the intraoral soft tissue, and that a separate suction line leads to the suction space bounded by the sealing wall, which suction line is connected to a separate vacuum connection piece that in turn is connected to a reduced pressure source, in particular to the reduced pressure source communicating with the impression space. The development of the invention according to this feature is advantageous having regard to a secure positioning of the tray in the patient's mouth at all stages of the impression producing procedure.

The passage cross-section of the connection elements for the impression material corresponds to the area of a circle having a diameter of about 2 to 8 mm, preferably about 4 to 6 mm. If the diameter of the connection elements of the tray is chosen according to this feature, this ensures a good reduced pressure charging in the impression space as well as a good supply of impression material to the interior of the tray.

The impression material source provides the impression material under excess pressure, preferably an adjustable excess pressure. The development of the invention according to this feature ensures an even more rapid filling of the impression space combined with a high impression accuracy.

The impression material source provides an impression material containing a hardening catalyst, the catalyst being chosen and metered and the reduced pressure in the impression space and the discharge pressure of the impression material source being adjusted relative to one another so that the hardening of the impression material takes place only after the impression space has been completely filled. Also, the development of the invention according to this feature is advantageous having regard to a tooth impression that is uniformly accurate in all sections.

There is a rinse fluid source that can be connected to the impression material connection element. With a device according to this feature the tray can also be used in order to rinse the impression space with a rinse fluid or treatment fluid before filling the space with impression material or in treatment situations that do not involve the production of impressions. This rinsing, may be carried out with liquid media as well as gaseous media.

The rinse fluid source provides a fluid containing at least one active constituent, for example a liquid containing active constituents or an active constituent aerosol or a gas. According to this feature, in conjunction with this rinsing procedure active constituents may also be allowed to act on the tooth surfaces or tissues, for example cleansing agents, separating agents or haemostatic agents, as well as the other treatment agents specified hereinbefore.

An impression material locking element is arranged at or in the vacuum connection elements. The development of the invention according to this feature ensures in a particularly effective way that no impression material reaches the reduced pressure source.

The impression material locking element contains a filter element. A closure element for impression material, as is specified in this feature, can easily be realised as a disposable part using conventional components.

The impression material locking element contains additional hardener material and/or additional catalyst material. The development of the invention according to this feature ensures that any impression material in a somewhat liquid state that still reaches the closure element cannot be sucked into the reduced pressure source.

The impression material connection element has a closure means. With a device according to this feature the impression space can first of all be evacuated in order to position the tray, without already having to connect for this purpose the source of the liquid hardenable impression material. This facilitates the positioning of the tray.

The closure means is a valve or a sealing foil that is forcibly opened when the source for the liquid hardenable impression material is connected to the impression material connection element. According to this feature the closure for the impression material connection element is achieved at low cost, and a simpler opening of the impression material connection element is immediately automatically ensured on connecting the source for the liquid hardenable impression material.

The tube wall of the impression material distributor tube has a plurality of outlet openings spaced apart in the longitudinal direction, which differ at least in some cases in their diameter and/or their alignment. The tube walls of the vacuum distributor lines have a plurality of outlet openings spaced apart in the longitudinal direction, which differ at least in some cases in their diameter and/or their alignment. The developments of the invention according to these features are advantageous having regard to the creation of the flow pattern of the impression material in the impression space. Preferably this flow pattern is adjusted so that the front of the impression material moves towards a still uncovered vacuum connection element until the filling procedure is completed. This means that in the practically advantageous arrangement of the vacuum elements in the front region of the tray, the mould is filled from back to front.

The invention is intended for use in a dental laboratory. The good dimensional accuracy of impressions that are obtained with the device according to the invention can advantageously also be utilised in the dental laboratory when making copies of impressions or parts thereof, as is specified in this feature.

When using the impression tray in the dental laboratory or for making copies or for other purposes, if no saliva or blood has to be removed, and where perhaps there are no wet gum surfaces and well-defined material surfaces to be treated, then the use of active vacuum suction can also be omitted. The vacuum connection elements then serve to aerate the impression space. The filling of the impression space is accomplished by introducing impression material under positive pressure.

The same comments also apply if the tray and/or the impression producing system is used only to carry out treatment with therapeutic agents.

The invention has a tray base part and a distributor part mounted on its external wall, that the tray base part has in its external wall at least one impression material feed opening and/or at least one vacuum feed opening spaced therefrom, and that an impression material feed channel arrangement is provided in the distributor part, which arrangement connects the impression material connection element carried by the distributor part to the impression material feed openings, and/or a vacuum feed channel arrangement is provided, by means of which at least one vacuum connection element carried by the distributor part is connected to the vacuum feed openings. An impression tray according to this feature is particularly simple to manufacture since the tray base part has substantially the same design and construction as a conventional impression tray. The only difference is that some additional feed openings are provided in the external wall. The addition of impression material to the impression material feed openings and the vacuum charging of the vacuum feed openings is effected by means of a distributor part mounted on the tray base part, which distributor part may in practice be an injection moulding or casting and may be inexpensively provided with the necessary channels.

At least one vacuum feed opening is provided in the anterior end section of the tray base part. At least one impression material feed opening is arranged in a distal end section of the tray base part. The developments of the invention according to these features are advantageous having regard to a particularly good guidance of the impression material in a constant direction without inclusion of bubbles.

The sections of the channel arrangements of the distributor part adjacent to the feed openings are formed as open grooves up to the tray base part. If the various channel arrangements via which the vacuum and impression material are supplied to the main part of the tray are formed at least partially as open grooves, according to this feature, then the distributor part is particularly simple to manufacture. These grooves together with the external surface of the tray base part form closed channels. This design of the channel arrangement is also advantageous having regard to effective disinfection and sterilisation as well as ease of cleaning after use.

The tray base part and the distributor part have cooperating positioning means. The development of the invention according to this feature ensures a necessary correct arrangement and alignment of the feed openings and channel arrangements.

The positioning means have positioning grooves and positioning ribs, which extend in the vicinity of the edges of the external wall of the tray base part. If extended positioning means according to this feature are chosen, then these do not need to have very sharply defined projections and recesses, which would be disadvantageous as regards cleaning the tray base part and the distributor part. Nevertheless, a reliable alignment of the distributor part on the tray base part is ensured.

The distributor part is detachably connected by means of an catch connection to the tray base part. The development of the invention according to this feature enables the distributor part and the tray base part to be combined into a single manipulable unit, which facilitates insertion into the mouth. Moreover, this ensures that the distributor part and the tray base part can also easily be separated from one another, and in addition these parts may also be made of different materials and using simple moulds.

The boundary surface of the distributor part facing the tray base part has at least one suction pocket that is connected via a further channel arrangement of the distributor part to a separate vacuum connection element. The development of the invention according to this feature ensures an even more chargeable connection between the tray base part and the distributor part.

At least one section of the tray base part is made of transparent material. With an impression tray according to this feature the dentist can visually check the filling of the impression space with impression material.

The feed openings and the channel arrangements are symmetrical relative to a longitudinal centre plane of the impression tray. With an impression tray according to this feature the filling of the impression tray takes place symmetrically.

Two vacuum connection elements are provided in the anterior end section of the distributor part, which elements communicate via a section of the vacuum feed channel arrangement with a central vacuum feed opening and preferably with two lateral vacuum feed openings approximately at the height of the canine tooth position of the tray base part. The development of the invention according to this feature ensures that if there is an accidental unsymmetrical filling of the impression space (due for example to gaps between the teeth), then when the liquid impression material reaches one of the vacuum connection elements, liquids are suctioned off as before through the other one of the vacuum connection elements and the still unfilled section of the impression space is subjected to a reduced pressure. As a result, during the filling of the impression space there is always a controlled flow of the impression material directed to at least one active vacuum feed opening, the accurate flow direction being predetermined by the curvature of the jaw and the position of the tooth.

The external surface of the distributor part is spherical. The development of the invention according to this feature is advantageous having regard to an overall sealing of the impression space area. The impression space is thus sealed not by the edges of the impression tray, but by soft tissue lying flat against the outside of the distributor part.

The tray base part and/or the distributor part is a plastics moulding. The development of the invention according to this feature is advantageous having regard to an inexpensive manufacture of the tray base part and the distributor part. These parts may be made as disposable parts if so desired.

The tray base part and/or the distributor part is a metal moulding. If the parts of the impression tray are made according to this feature of metal, then these parts can be sterilised and reused.

The various connection elements are arranged closely adjacent in the anterior end section of the distributor part. The development of the invention according to this feature enables all connection joints between the impression tray and vacuum source and/or impression material source to be effected by a single multiple connector. This simplifies the use of the impression tray.

The vacuum feed channel arrangement has, looking in the flow direction, at least one impression material lock in front of at least one vacuum feed opening. With the development of the invention according to this feature, at least one of the vacuum feed openings is in communication with a vacuum connection piece up to the completion of the filling of the impression space. This development also prevents closed channels of the distributor part being filled with impression material, which could be removed only with great difficulty.

The impression material locks are in each case formed by a raised section of the floor of a distributor groove, which is part of the vacuum feed channel arrangement. According to this feature an impression material lock can be produced in a particularly simple manner during the injection moulding, casting or machining of the distributor part.

The tray has a feed opening communicating with a first end of the impression space and a second feed opening communicating with a second end of the impression space. With the development of the invention according to this feature the impression material successively fills, starting from one end and going to the other end, the mould space bounded by the tray and soft tissues. The addition of impression material can then be stopped once a particular part of the dentition in question is surrounded by impression material, by visually checking the movement of the front of the impression material. The rest of the impression space remains unfilled. A significant saving in impression material is achieved in this way.

In the dental laboratory it is sometimes necessary to produce a negative mould from a tooth model that was made starting from a tooth impression or from models with intermediate stages mounted thereon in the production of replacement teeth or in teeth restoration work, prostheses, implants, explants, etc. This work is termed copying or replication.

In the present description the term copying should generally be understood to mean making copies of arbitrary surface sections of dental, dental-medical or medical objects, in particular moulded bodies, outside the mouth, for example of sections of model surfaces or replacement tooth surfaces or prosthesis surfaces, implant surfaces, explant surfaces, etc. If very accurate model impressions obtained by copying are required, similar problems to those that arise in making impressions of teeth are encountered. The device according to the invention for producing tooth impressions can therefore also be used to produce model impressions, and accordingly in copying. Of course, in addition to the tray a cavity or lower mould is also required that is comparable as regards its mechanical properties to the soft tissues in a patient's mouth, and can therefore define in particular together with the tray a flow medium-tight impression space. A device with such a cavity mould constitutes the subject matter of the following feature: there is a cavity mould on which an object of which an impression is to be made can be secured, and which has a preferably deformable sealing wall surrounding the object of which an impression is to be made, which together with the tray defines a sealed impression space.

The sealing wall has a sealing membrane secured on a housing of the cavity mould. This feature discloses a particularly simple way and means of preparing a sealing wall that accurately matches the edge contour of the tray.

The sealing membrane together with the housing defines a membrane rear space that is filled with a fluid. The development of the invention according to this feature enables the deformability of the sealing wall to be modified in a simple way, by altering the nature or the pressure of the fluid lying behind the sealing membrane.

The corresponding variants are disclosed in the following features: the fluid is a gas under reduced pressure, whereby the sealing membrane is prestressed into a concave shape; the fluid is a liquid or a gel; and there is a pressure regulator communicating with the membrane rear space.

The sealing wall comprises elastically deformable material. According to this feature a sealing wall is also obtained that can accurately match the edge contour of the tray, this sealing wall requiring no separate clamping arrangement or indeed any connection to a vacuum or pressure source.

The free front surface of the foam material has a tight surface skin or carries a film impermeable to flow media. The development of the invention according to this feature is advantageous having regard to a particularly simple construction and fluid-tightness of the sealing wall.

The tray has an external circumferential wall that is adjustable as regards height. The development of the invention according to this feature enables impressions to be made from models of different heights, with a saving in the use of impression material.

The circumferential wall has a stationary wall part and a vertically movable wall part in a groove of the latter, as well as means for predetermining the spacing between the movable wall part and stationary wall part. The development of the invention according to this feature enables the height of the tray to be continuously adjusted.

The movable wall part is pretensioned in an extended position by means of a spring arrangement. If the tray is designed according to this feature, it always adopts the same position in the state in which it is not yet mounted on the mould lower part. This facilitates a precise positioning and furthermore protects the sealing wall of the mould lower part when the tray is mounted.

The movable wall part is sealed by a sealing arrangement against the groove of the stationary wall part. The development of the invention according to this feature ensures that no impression material reaches the guide for the movable wall part.

The tray is a one-pieced disposable part made of plastics material, in particular a deep-drawn part. The development of the invention according to this feature is advantageous having, regard to ensuring hygienic conditions without the use of sterilisation processes.

At least one feed opening of the tray that can be connected to a vacuum source is arranged in an, under operating conditions, upper wall section of the tray. The development of the invention according to this feature serves for a bubble-free complete filling of the impression space.

At least one of the feed openings is provided in an, under operating conditions, rear wall of the tray. The development of the invention according to this feature enables the impression material, in the production of model impressions, to flow in from the rear end of the model without having to provide the tray with a system of channels.

If the tray used for making the impressions is rigid, then a strictly predetermined amount of impression material is required to produce an impression. The tray has a bowl-shaped rigid tray housing and an elastically deformable impression space membrane secured to the latter. When using a tray according to this feature the impression space membrane partially defining the impression space can be matched as regards its geometry to the space occupied by the model, so that the impression includes only the space regions of interest that are immediately adjacent to the model.

There are means for contouring the impression space membrane. With the development of the invention according to this feature a pre-contouring is imparted to the impression space membrane.

The contouring means have a contoured supporting element and means for pretensioning the impression space membrane against the supporting element. With the development of the device according to this feature the pre-contouring of the impression space membrane can be reproduced very accurately.

The supporting element is lattice-like or open-pore and the pretensioning means have a reduced pressure source that can be connected to the working space bounded by the impression space membrane and the tray housing. According to this feature the impression space membrane is urged flat against the contoured supporting element by applying a reduced pressure.

The pretensioning means have a pressure source that can be connected to the impression space in front of the impression space membrane. According to this feature the same advantage is obtained using an excess pressure source, in which connection the latter may for example be an impression material source that delivers the impression material under excess pressure.

The tray has an impression space membrane running over the model and means are provided for subjecting different regions of the impression space membrane to different loads, the impression space membrane preferably being secured to a lower section of a housing of the cavity mould. Also, the development of the invention according to this feature permits a simple matching of the geometry of the impression space to the size of a model of which an impression is to be produced.

The loading means have weights adapted to different regions of the model. According to this feature the force that the membrane exerts against the added impression material can be predetermined in a simple way, and the wall thickness of the impression can be varied by selecting different weights.

The loading means have at least one position indicator cooperating with one of the weights. According to this feature the manner in which the impression material increasingly flows round the model can be measured, and after the material has reached a predetermined height above the tip of the model the addition of further impression material can be stopped.

There is at least one dead space element inserted in the tray, which is chosen from a plurality of standard dead space elements or is plastically deformable. Also, the development of the invention according to this feature is advantageous having regard to savings in the use of impression material, particularly when producing partial impressions that extend over only a part of a jaw.

BRIEF DESCRIPTION OF THE DRAWINGS

The invention is now described in more detail hereinafter with the aid of embodiments and with reference to the accompanying drawings, in which:

FIG. 22: Is a developed representation of the inside of a distributor part of an impression tray according to FIGS. 19 to 21;

DETAILED DESCRIPTION OF THE INVENTION

Figure 1:
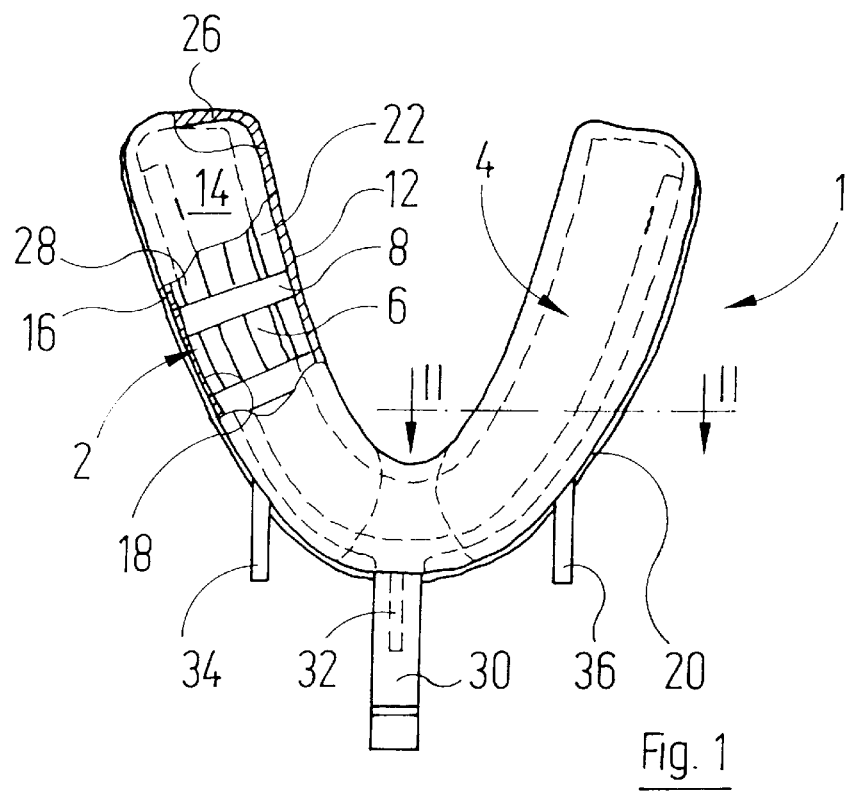
FIG. 1: Is a plan view of a tray for producing a lower jaw impression.
Figure 2:
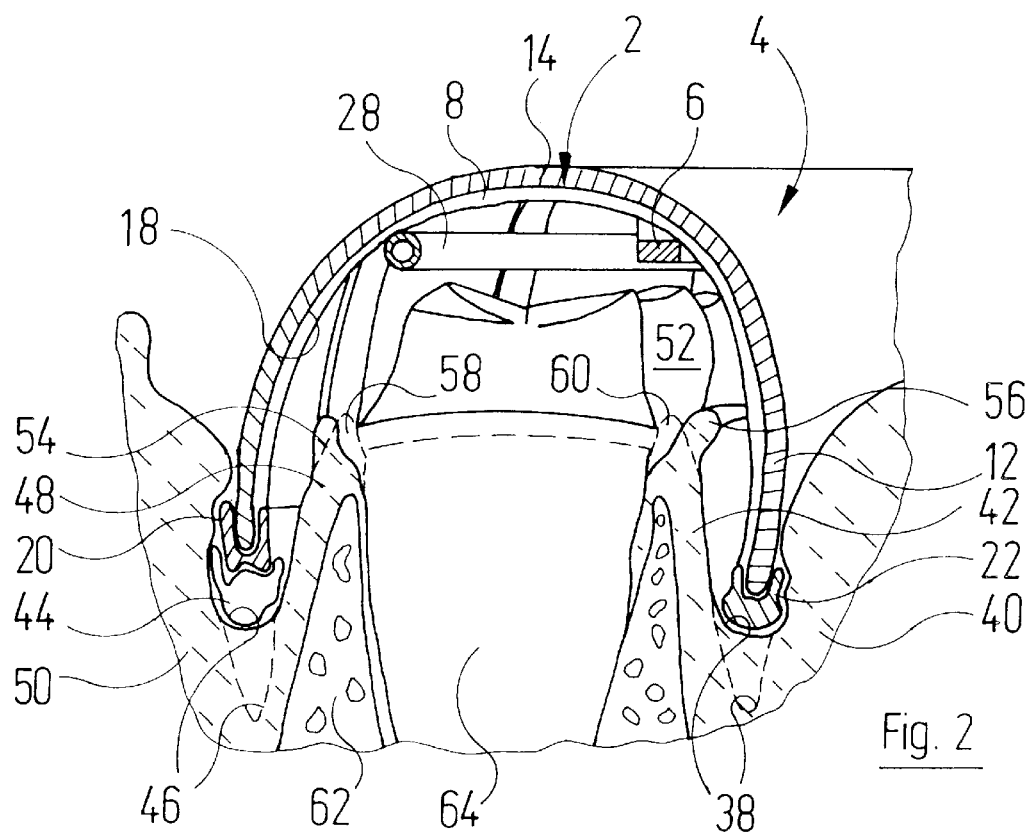
FIG. 2: Is a transverse section through the tray according to FIG. 1 along the section line II—II on an enlarged scale, the tray being positioned in the patient's mouth over the lower jaw teeth.

In FIGS. 1 and 2 a tray for producing an impression of the lower jaw dentition of a patient is denoted overall by the reference numeral 1. In plan view the tray has the shape of a parabola or, more simply, a V or U, whose arms form an angle of about 50° relative to one another and are slightly curved, as can be seen from the drawing. In this way the tray roughly matches the contour of a lower jaw.

An upper jaw tray on the other hand has an approximate elliptical shape.

The size of the tray is governed by epidemiological data and frequency distributions of different jaw sizes. In practice it may be sufficient to provide three different standard tray sizes for both the upper jaw and lower jaw.

The tray 1 comprises a rigid cage-like skeleton 2 and a transparent cap part 4, preferably a disposable plastics part, lying thereabove. The skeleton 2 includes a (seen in plan view) U-shaped bent rail 6 on which transverse ribs 8 are secured.

In transverse sectional view the cap part 4 is substantially U-shaped. An internal wall 12 is connected via an arcuate base wall 14 to an external edge wall 16. These together define an impression channel 18.

Sealing strips 20, 22 that at the same time form longitudinal ribs of the skeleton 2 are firmly mounted on the free ends of the ribs 8 lying underneath under operating conditions. These strips extend up to the transverse front walls 26 at the ends of the arms of the tray 1.

The sealing strips 20, 22 may be manufactured, at least in sections, of a soft material.

A U-shaped distributor tube 28 runs along the external edge wall 16. This tube has a central section formed as a T-piece and carried by the edge wall 16. This section communicates with a connection piece 30 that under operating conditions is joined to a source for liquid impression material.

In FIG. 1 a connection piece 32 that is connected to a reduced pressure source is provided underneath the connection piece 30. Two further vacuum connection pieces 34, 36 are provided symmetrically on both sides of the longitudinal centre plane of the tray 1. These pieces lie in each case mesially of the canine teeth, between the canine tooth and the lateral incisor.

FIG. 2 shows one of the aforedescribed trays under working conditions in a patient. The internal sealing strip 22 sits in an envelope fold 38 lying between the tongue 40 and the gum 42 on the tongue side.

The external sealing strip 20 is supported in the application under consideration here via a plastic sealing body 44 on the floor of a buccal envelope fold 46 lying between the buccal gum 48 and the buccal tissue 50. The sealing body 44 may for example be a wax filament, a flexible tube, a shaped silicone composition, a permanently soft plastics material, a cotton wool plug, a plastically worked plastics material shaped intraorally on the tray in situ and that hardens in a thermosetting manner (production of an individualised tray), or the like.

The front walls 26 or sealing bodies optionally provided thereunder and corresponding to the sealing bodies 44 closely cooperate with the jaw sections covered with soft tissue lying behind the teeth. In this way the tray 1 as a whole together with the tissues adjacent to the teeth define a flow medium-tight impression space 52.

Under working conditions the impression space 52 is connected via the connection pieces 32 to 36 to a reduced pressure source. When the soft tissues are subjected to reduced pressure they are brought from their normal state shown by the dotted line in FIG. 2 to the state shown by the full lines. In this latter state the edges 54, 56 of the periodontal region adjacent to the neck of the tooth are retracted from the neck of the tooth so that this is open via the gap 58, 60 up to the impression space 52.

62 denotes the bony alveolar process. 64 shows a prepared lower jaw molar.

If the connection piece 30 is connected under the conditions illustrated in FIG. 2 to a source for liquid impression material of higher viscosity compared to water ("thin-bodied" impression material), this flows primarily under the feed pressure predetermined by the impression material source, but also assisted by the reduced pressure prevailing in the impression space, into the impression space 52 including the gap 58, 60, and fills these completely, the front of the liquid impression material displacing before it liquids (water, saliva, blood) present in the impression space 52, so that these liquids cannot form any bubbles in the impression. The liquids are suctioned off through the connection pieces 32 to 36.

After the impression material has hardened a very precise and accurately fitting impression of the lower jaw dentition is obtained, especially also in the region of the gum edges.

The tray 1 is a rigid part manufactured at least partially (cap part 4 or part thereof) of transparent material. In this way the progress of the filling of the impression space 52 with an impression material, which is preferably coloured, can be visually easily followed.

Details of the preferred working conditions for producing an impression and impression materials that may be used for this purpose are described in more detail hereinbelow.

Figure 3:
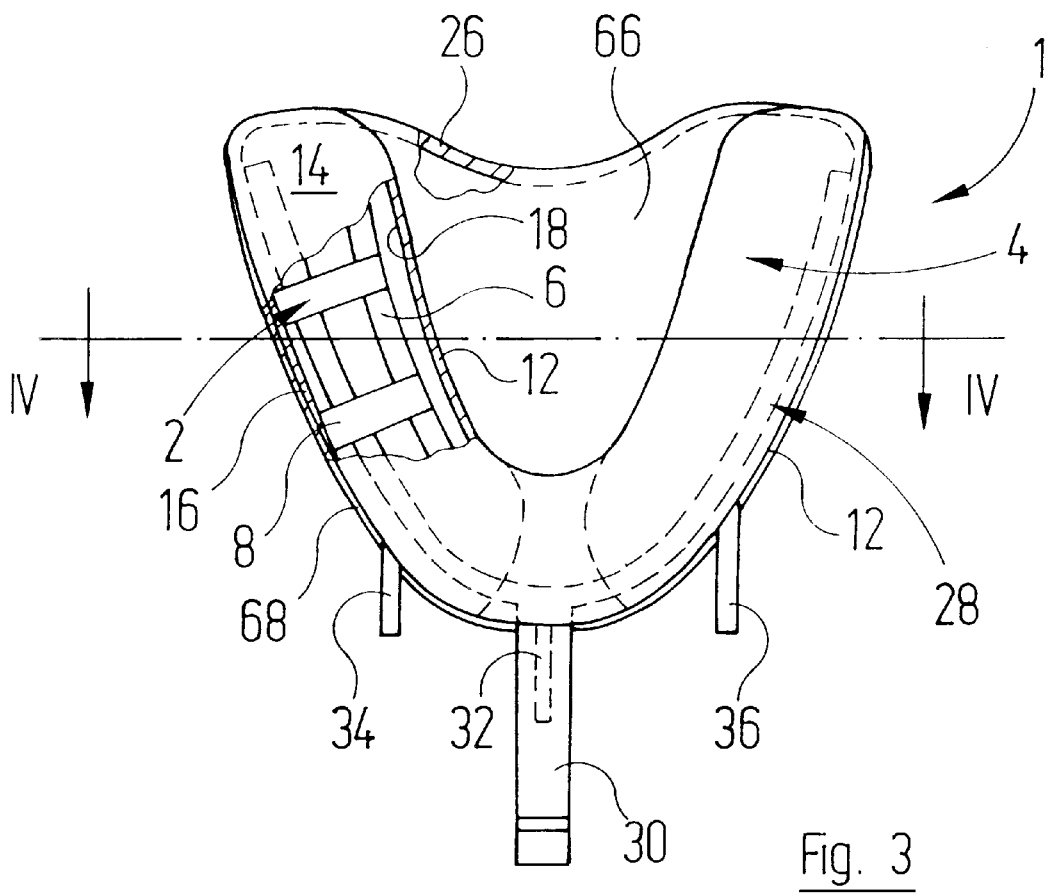
FIG. 3: Is a plan view of the underneath of a tray for producing an upper jaw impression.
Figure 4:
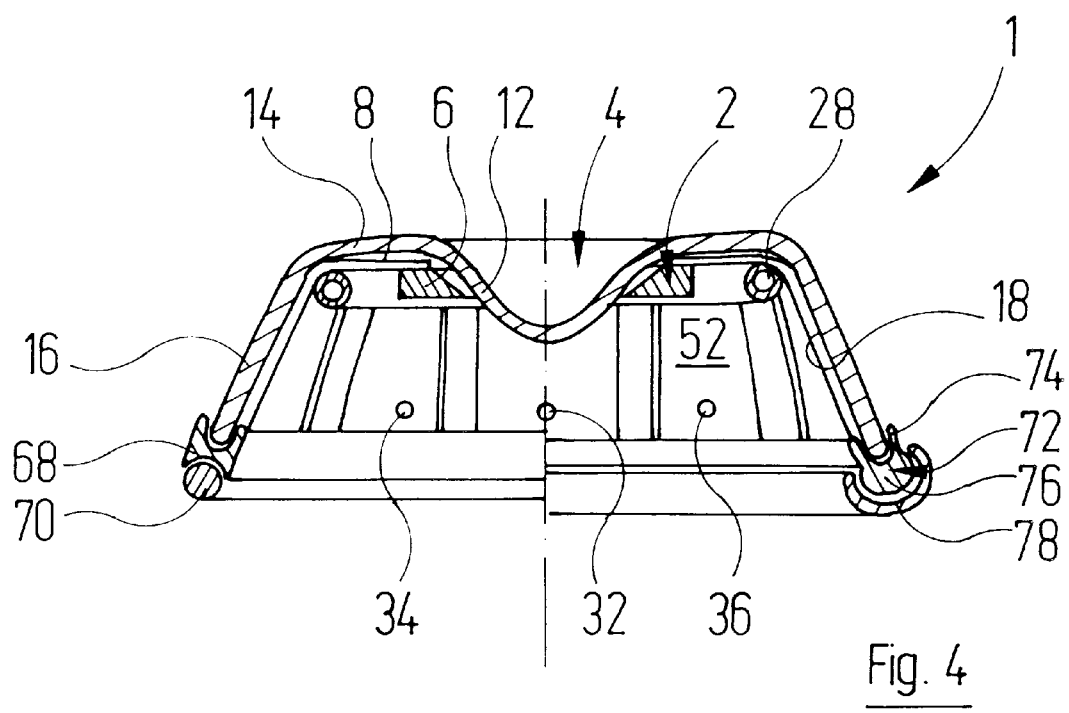
FIG. 4: Is a transverse section through the tray according to FIG. 3 along the section line IV—IV.

FIGS. 3 and 4 show a similarly constructed tray 1, which however is used for producing an impression of an upper jaw. Parts having a comparable function are again provided with the same reference numerals. The tray 1 according to FIGS. 3 and 4 differs primarily from that according to FIGS. 1 and 2 in that it additionally has a central wall 66 that copies the contour of the soft palate, and more specifically by the fact that it is at a mean distance of 1 to 2 cm from the latter. Moreover, the tray 1 according to FIGS. 3 and 4 differs from that according to FIGS. 1 and 2 by its modified cross-sectional shape, as can be seen from the drawing.

As regards the free edges of the tray 1, two different sealing arrangements are shown in FIG. 4 to the right and left of the mid line. The left-hand section of FIG. 4 shows a sealing strip 68 having a substantially H-shape cross-section and connected to the transverse ribs to form a skeleton, the said strip accommodating the free edge of the edge wall 16 between its upper arms, while its lower arms accommodate a deformable cylindrical sealing element 70.

In the right-hand half of FIG. 4 a sealing strip 72 that is likewise connected to the transverse ribs to form a skeleton is mounted on the free edge of the edge wall 16, which strip accommodates the edge wall between its arms 74 and has a head section 76 of circular cross-section, on which is arranged a sealing element 78 of C-shaped cross-section.

Such a multi-layered arrangement of the sealing points between the tray and tissue may be advantageous having regard to compensating relatively large geometrical differences, for which purpose the external sealing elements 70 and/or 78 are used as necessary by the dentist, though several sealing elements 78 on top of one another may also be used.

In the case of the trays shown in FIGS. 1 to 5 the cap part 4 may also be made of a weaker material since there exists of course the rigid framework-like supporting structure in the form of the loadable rails 6 and the ribs 8 as well as the sealing strips 20, 22 and 68, 72 connected thereto, which extend in the longitudinal direction of the impression channel 18 and are firmly wholly or partially embedded in the impression material when producing an impression of the jaw. If the sealing strips are made of soft material, they do not contribute to the rigidity of the tray. However, in this case too it is ensured that the hardened impression material together with tray sections embedded therein forms a stable rigid structure.

In this case the tray itself may also be made of plastics or as a moulded film (for example vacuum-shaped polypropylene film) instead of glass. If the advantage of the visual contact with the interior of the impression space is dispensed with, the tray may also be made of metal.

By way of modification of the aforedescribed embodiments the tray may also be formed as a single-piece disposable part or may be composed of more than two tray parts. Impression trays consisting of two or more parts have the advantage that one of the tray parts is designed as a universally usable standard part, while a fine matching of the size to the jaw of the respective patient may be made in other parts of the tray. This matching is preferably carried out in a tray part designed as a disposable part.

Figure 5:
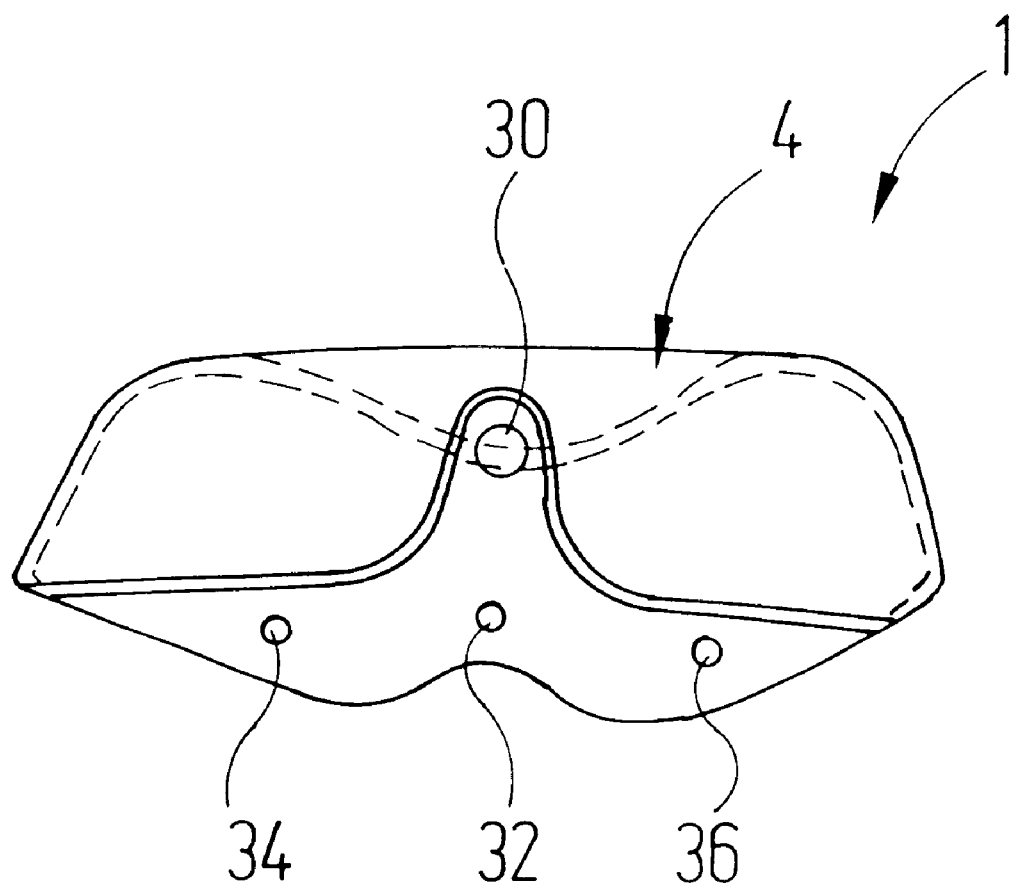
FIG. 5: Is a front view of the tray according to FIGS. 3 and 4.
Figure 6:
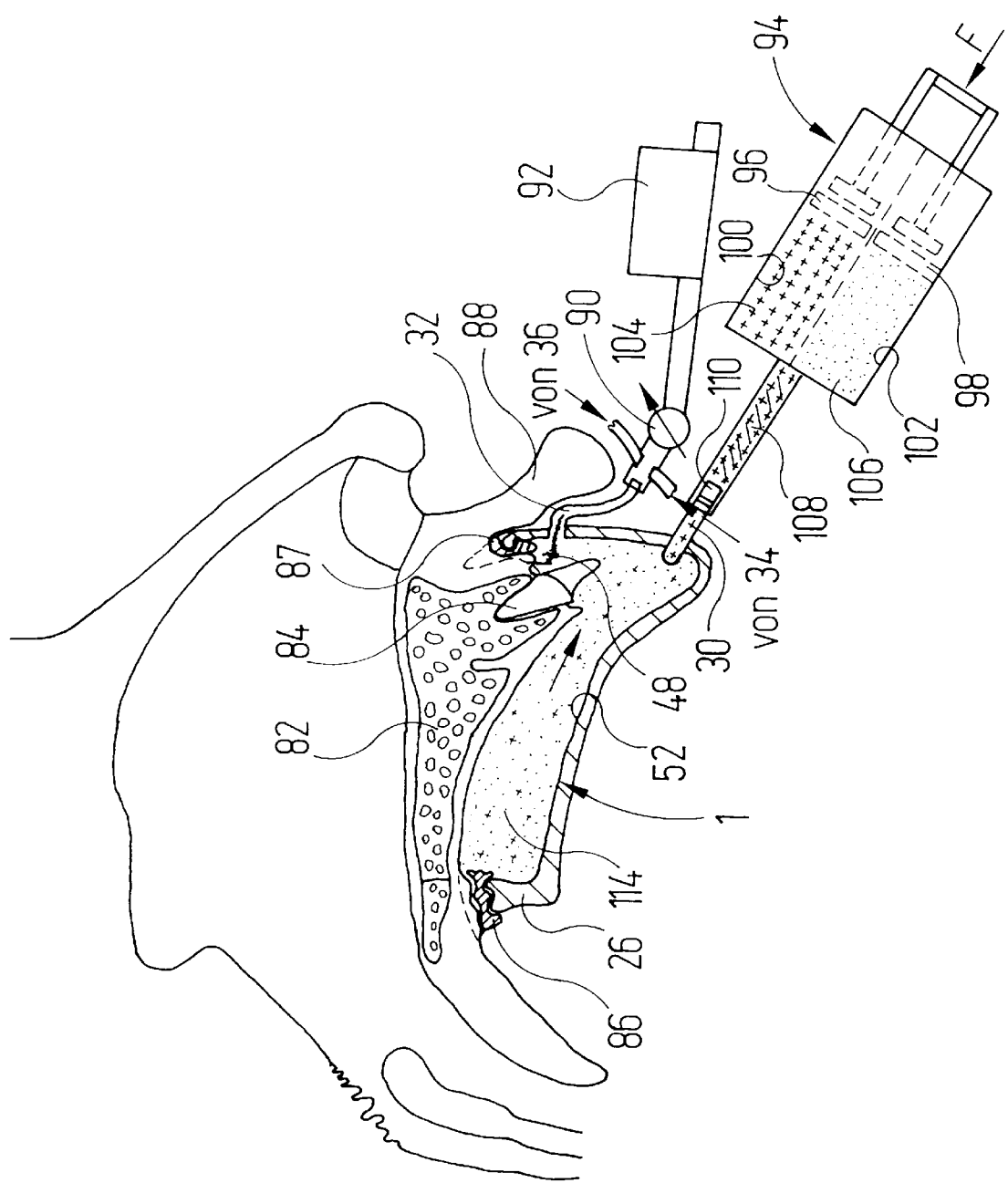
FIG. 6: Is a section through the nose, mouth and throat region of a patient, on the basis of which the use of a tray according to FIGS. 3 to 5 is illustrated.
Figure 7:
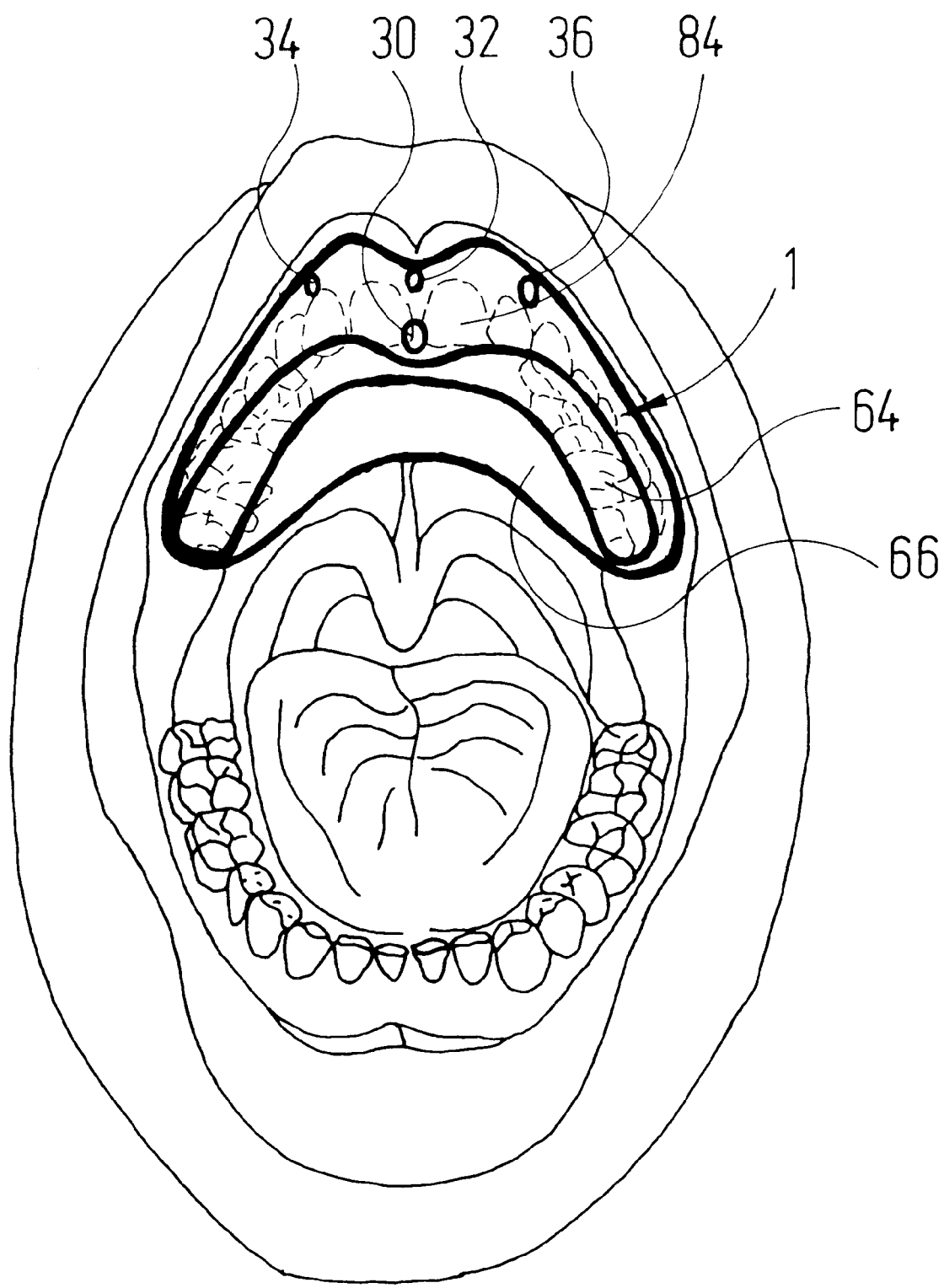
FIG. 7: Is a plan view of the underneath of the tray according to FIGS. 3 to 5 under working conditions.
Figure 8:
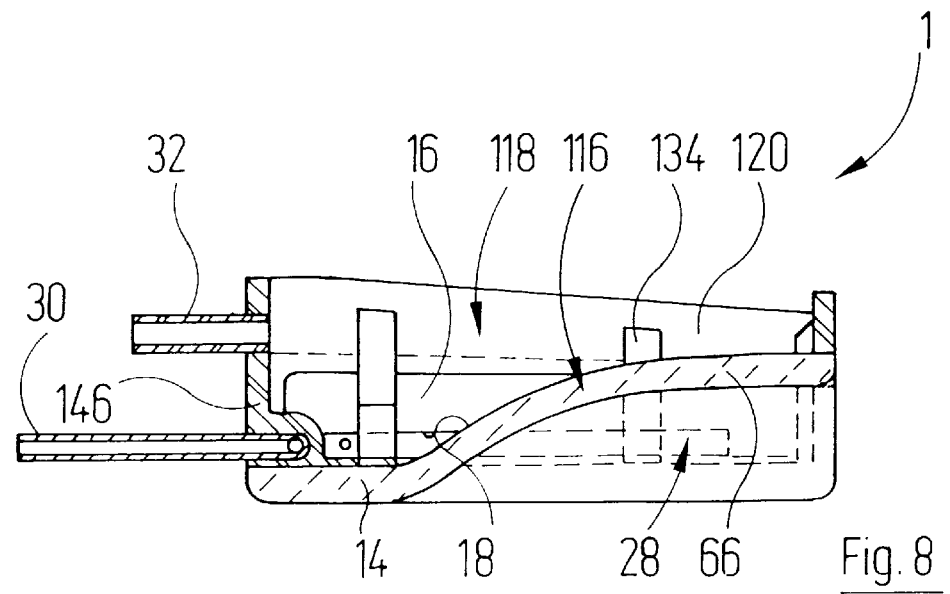
FIG. 8: Is a section taken in the longitudinal centre plane, through a modified tray.
Figure 9:
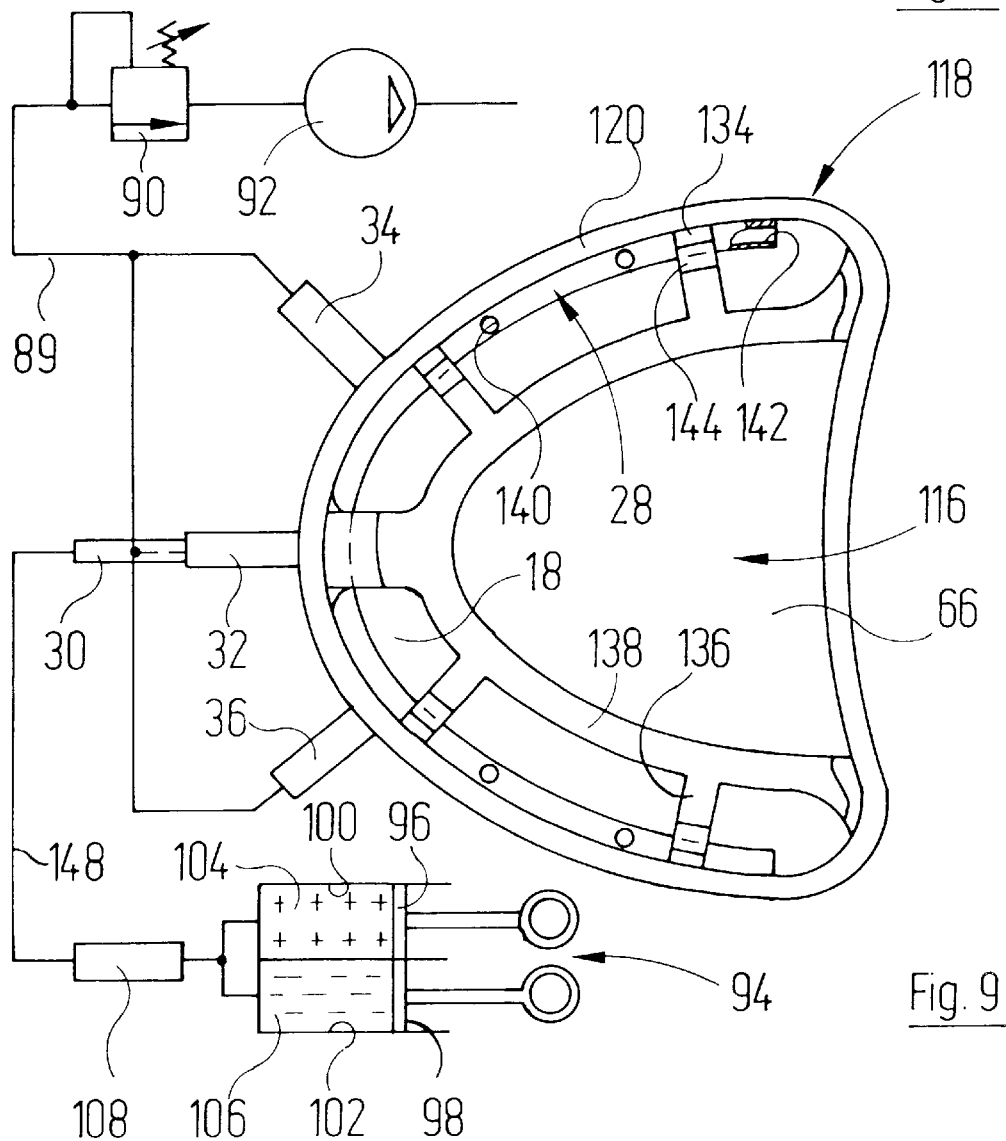
FIG. 9: Is a plan view of the upper side of the tray according to FIG. 8 as well as a schematic representation of the supply arrangements associated with the tray for producing an impression.

FIGS. 6 and 7 show the tray according to FIGS. 3 to 5 under conditions of use.

In the sagittal section according to FIG. 6, the hard palate of a patient is denoted by the reference numeral 82. A prepared incisor is denoted by the reference numeral 84.

A plastically deformable sealing compound 86 is shown underneath the free edge of the rear end wall 26 of the tray 1, and the front section of the edge wall 16 sits (optionally with the interposition of a sealing body 87) in that region of the envelope fold 38 located between the upper lip 88 and the external labial gum 48.

The three vacuum connection pieces 32, 34, 36 are connected via a common vacuum line 89 and a reduced pressure regulator 90 to the suction side of a suction arrangement 92. The impression material connection piece 30 is connected to the outlet of a tandem syringe 94, whose plungers 96, 98 may be operated separately or together as desired. The two cylinders 100, 102 of the tandem syringe contain a liquid binder 104 and/or a liquid hardener 106 containing a catalyst. The two cylinders 100, 102 communicate with a mixer 108, which may for example include a mixing tube with mixing screws arranged therein. A valve 110 is shown at the inlet of the connection piece 30, the valve being closed when the tandem syringe 94 is not connected up, so that under these conditions a vacuum can be produced in the impression space 52 in order to position the tray 1 reliably on the upper jaw. When the tandem syringe 94 is connected up the valve 11 is then opened. Alternatively a shaped membrane may be provided on the impression material connection piece 30, the membrane being perforated when the tandem syringe 94 is connected up.

Again by way of modification a separate mixing device may be used instead of a tandem syringe 94 with connected mixing tube, and a simple syringe may be filled with already mixed material and then connected up to the impression material connection piece 30.

FIG. 6 shows an advanced stage in the filling of the tray with impression material. The impression material is conveyed through the U-shaped distributor line 28 running in the interior of the tray 1, to the rear ends of the arms of the impression channel 18. On account of the force exerted on the plungers 96, 98 the impression material is forcibly introduced into the impression space 52 and increasingly forced forwards.

During the filling of the impression space 52 from the rear to the front, the front surface of the liquid impression material displaces saliva or blood residues forwardly to the vacuum connection pieces 32, 34, 36. The increasing filling of the impression space 52 by the impression material 114 dispensed by the mixer 108 can be visually checked if the cap part 4 has been made of a transparent material. In particular, the filling can be visually checked when impression material enters the transparent vacuum connection pieces 32, 34, 36. When all these three pieces are filled with impression material, the movement of the plungers 96, 98 can be stopped.

The hardening characteristics of the impression material 114 are selected via the choice of the hardener 106 and the catalyst and/or inhibitor contained in this and/or in the binder, so that the impression material is still perfectly fluid until the impression space 52 is completely filled. After the impression material has hardened and the connections to the connection pieces 30 to 36 have been released, the tray 1 can be removed from the upper jaw in a manner known per se, the connection pieces 30 to 36 serving, at the same time as gripping means.

As is clear in particular from FIGS. 5, 6 and 7, the vacuum connection pieces 32, 34, 36 all lie at the level of or apically relative to the neck of the tooth in the region of the envelope fold. The two lateral connection pieces lie in a tangential extension to the side teeth, the middle connection piece lying between the two middle incisors. This arrangement ensures that the tray is reliably filled also in the case where the dental arch is asymmetrical.

In the modified tray according to FIGS. 8 to 11 a tray base part 116 is provided that is formed as a rigid glass body or rigid transparent plastics body. The tray base part substantially corresponds as regards its basic geometry to the tray 1 according to FIGS. 3 to 5, though its external edge wall 16 is slightly lower. A tray edge part denoted overall by the reference numeral 118 is mounted on the tray base part 116. This edge part has an external edge wall 120 that forms a continuous extension of the edge wall 16 of the tray base part 116. As can be seen from FIG. 10, a sealing point may be produced between the edge walls 16 and 120 by forming an upwardly projecting, external tongue 122 on the upper end of the edge wall 16, while the edge wall 120 has an internal, downwardly projecting tongue 124 that cooperates with the tongue 120 in the manner of a tongue/groove joint.

Figure 10:
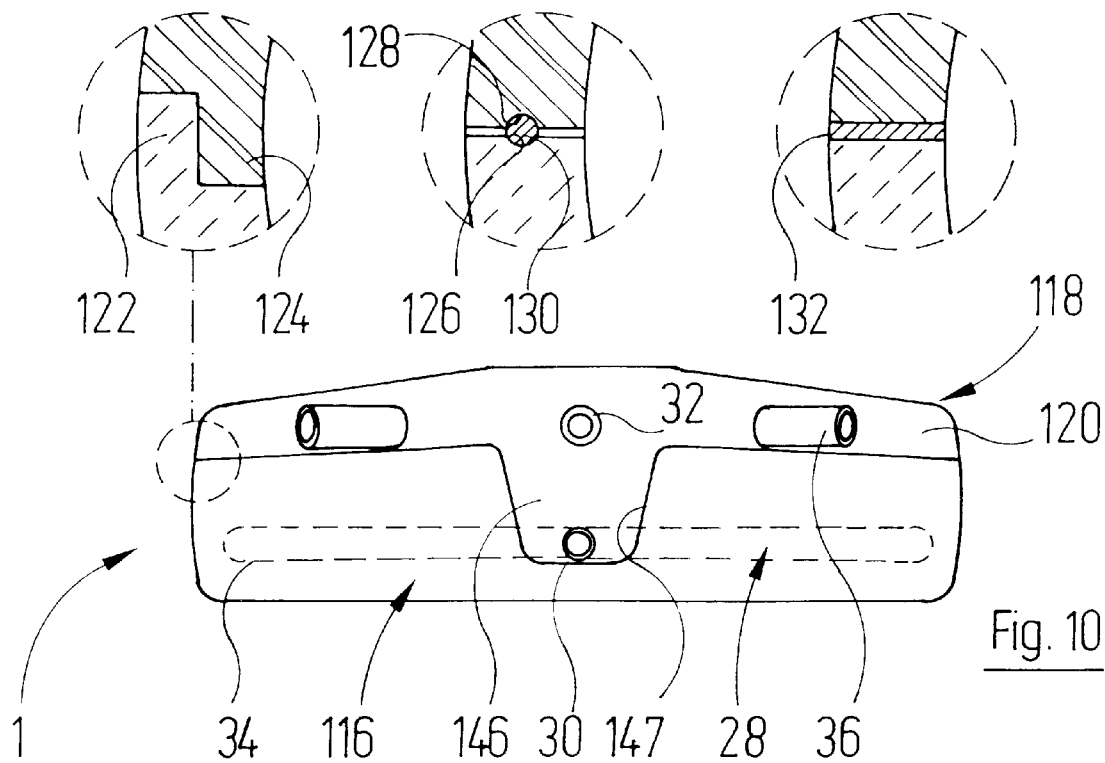
FIG. 10: Is a front view of the tray according to FIGS. 8 and 9.
Figure 11:
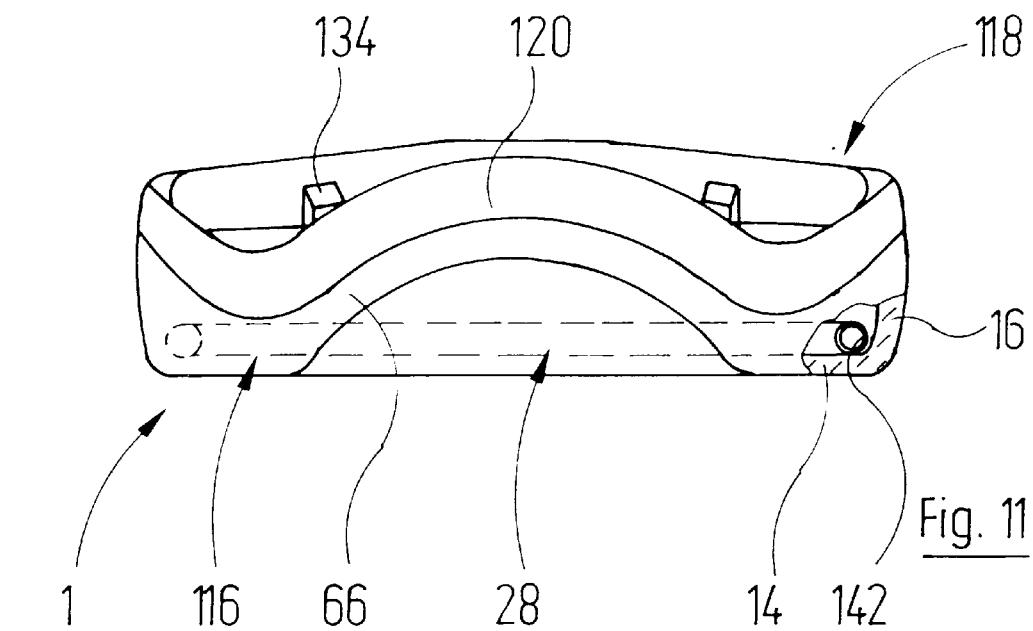
FIG. 11: Is a plan view of the rear side of the tray according to FIGS. 8 to 10.

Alternatively, as is also shown in FIG. 10, in the front surfaces of the edge walls 16 and 120 there may be provided aligned grooves 126, 128 in which engage in each case a section of a seal 130.

Likewise, the two front surfaces of the edge walls 16 and 18 may if desired also be joined by a plastics sealing compound or adhesive 132.

It is understood that the aforementioned alternatives for producing a tight connection between the edge walls 16 and 120 may also be combined with one another.

Various vertical webs 134 projected downwardly from the edge wall 120 of the tray base part 118. These webs are connected to radially extending transverse webs 136, whose radially directed internal ends carry an internal longitudinal web 138. The edge wall 120 and the webs 134, 136 and 138 thus form overall a cage-like structure by means of which the tray edge part 118 is stiffened.

In the embodiment considered here the U-shaped distributor tube 28 leading to the rear ends of the impression channel 18 is provided in its two arms with respectively two outlet openings 140 lying in the central arm section, not directly aligned towards the teeth and optionally also pointing away from the teeth. By virtue of this arrangement of the distributor tube 28, already at the beginning of the filling phase liquid impression material is conveyed to the front section of the impression space 52.

The size of the outlet openings 140 provided in the wall of the distributor tube 28 and the size of the open rear end 142 of the distributor tube 28 are however chosen having regard to the viscosity of the liquid impression material, so that the filling of the impression space furthermore primarily takes place from the rear to the front, and thus in the direction of the vacuum connection pieces 32, 34, 36.

As is clear from the drawing, the distributor tube 28 is embedded in thickened feet sections 144 that lie at the lower ends of the vertical webs 134.

The tray edge part 118 is preferably made of transparent plastics material so that, as already described hereinbefore with reference to FIGS. 1 to 7, the retraction of the gum edges from the necks of the teeth by application of a suitably large reduced pressure and the filling of the impression space 52 can be visually followed. Also, the vacuum connection pieces 32 to 36 are again made of transparent plastics material, and are preferably formed on the tray edge part 118.

Alternatively, the vacuum connection pieces 32 to 36 can also be made only partially transparent or can be joined by transparent connection pieces to the common vacuum line 89.

As is clear from FIG. 10, the tray edge part has in its central, front section a downwardly hanging apron 146 into which the impression material connection piece 30 communicating with the distributor tube 28 is inserted and which engages in a recess 147 in the edge wall 16. In this way all flow medium connections and all channels distributing the flow medium are located on the tray edge part 118 and form together with the latter an inexpensive disposable part. The rigid, torsion-free section of the tray, namely the tray base part 116 made of for example glass or transparent plastics material, is on the other hand free of elements that are difficult to clean. The tray base part 116 can thus be reused after sterilisation.

In a further development of the invention the various connection pieces can be combined to form a common connector (optionally multi-part connector).

In a modification of the aforedescribed embodiment the distributor tube 28 may also be replaced by a downwardly open distributor channel of C-shaped cross-section and formed on the tray edge part 118, which together with the floor of the impression channel 18 defines a distribution channel.

The tray described above with reference to FIGS. 8 to 11 is used as follows:

First of all a disinfected and/or sterilized tray base part 116 together with a disposable tray edge part 118 is assembled, optionally using a sealing compound, to form a tray 1 as illustrated in FIGS. 8 to 11. This tray is placed in position under visual monitoring on the patient's upper jaw. When the correct position is achieved the reduced pressure regulator 90 is coarsely adjusted to a value at which the tray is immovably positioned by suction to the soft tissues surrounding the upper jaw dentition. Under further visual monitoring the reduced pressure is then increased until the gum edges are slightly retracted from the neck of the teeth, as has already been explained hereinbefore with reference to FIGS. 1 to 7. The reduced pressure regulator 90 then maintains this pressure reduction, which is as a rule between 10 and 500 mbar, preferably between 10 and 200 mbar, and particularly preferably between 50 and 150 mbar.

The valve 11 is now opened by attaching the impression material feed line 148 coming from the mixer 108, to the connection piece 30, and the liquid impression material flows under the pressure exerted on the plungers 96, 98 and with the cooperation of the reduced pressure prevailing in the impression space 52, through the distributor tube 28 and flows out through its open rear ends 142 and, if present, the outlet openings 140. The impression space 52 fills up again from the rear to the front with impression material, which forwardly displaces saliva and blood to the connection pieces 32, 34, 36. When the liquid impression material has reached all three connection pieces 32, 34, 36 the force exerted on the plungers 96, 98 can be stopped. The feed line 148 is then removed from the connection piece 30, whereupon the valve 11 incorporated therein recloses.

After the impression material has hardened the reduced pressure regulator 90 is then reset to the locking initial position, and the tray 1 can now be removed from the upper jaw dental arch.

If desired, the reduced pressure charging of the tray can also already be terminated after the impression space 52 has been completely filled.

Figure 12:
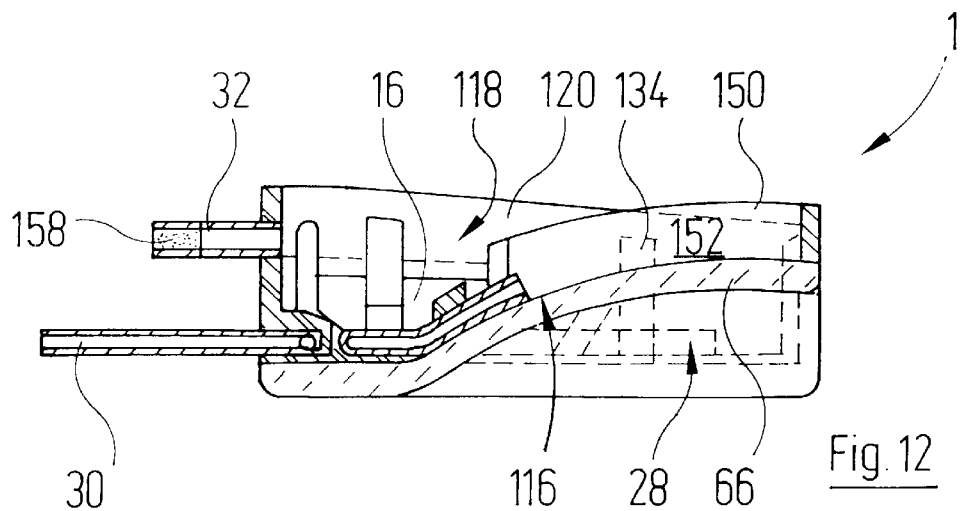
FIG. 12: Is a longitudinal section through a further modified tray for producing an upper jaw impression.
Figure 13:
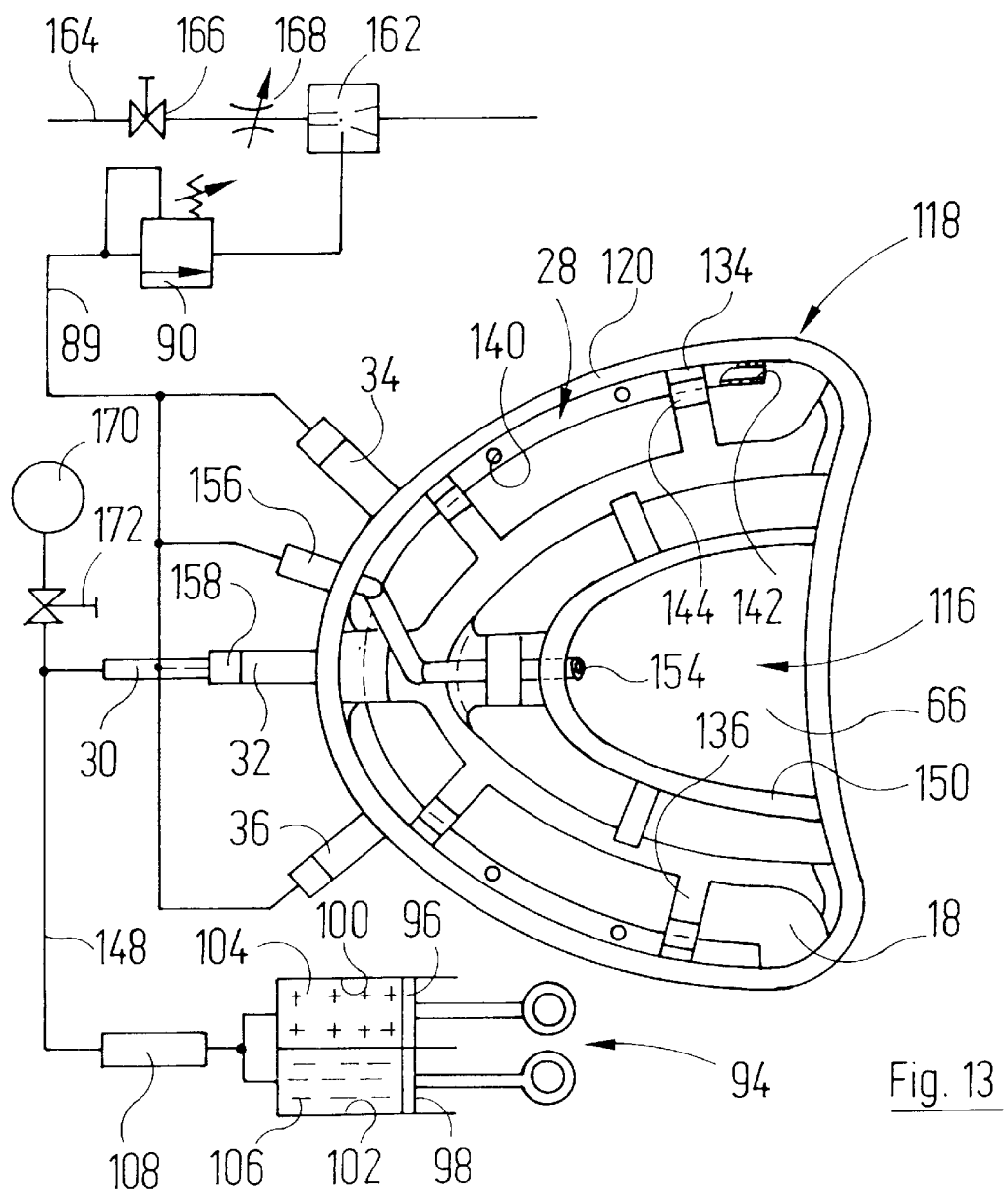
FIG. 13: Is a plan view of the upper side of the tray according to FIG. 12.

The embodiment according to FIGS. 12 and 13 of the drawings differs from the embodiment that has just been described in that the central wall 66 of the tray 1 running at a distance from and parallel to the soft palate carries an additional sealing wall 150 whose free edge can be applied tightly against the soft palate. The suction space 152 defined under operating conditions by the sealing wall 150 and the soft palate communicates via a separate suction line 154 to the reduced pressure regulator 90. In this way it is ensured that the tray 1 is also still pressed against the patient's upper jaw under a strong suction effect when the impression space 52 has already been completely filled with impression material, or also in the case where liquid, aerosol-type or gaseous rinse media or therapeutic agents are dispatched through the impression space 52.

In the embodiment according to FIGS. 12 and 13 cylindrical filter elements 156, 158, 160 are in addition attached to the connection pieces 32, 34, 36, which elements are blocked by liquid impression material that has for example been sucked into them. In order to improve the locking effect still further the actual filter surfaces of the filter elements may be provided with additional hardener or catalyst material or with inhibitor antagonists.

Furthermore, in the embodiment according to FIGS. 12 and 13 a Venturi nozzle 162 may be provided in place of a suction device (compressor). The reduced pressure connection of the nozzle is connected to the reduced pressure regulator 90, and its feed inlet communicates via an on-off valve 166 as well as a throttle valve 168 with a compressed air line 164. In this way the reduced pressure necessary for operating the tray 1 can be Generated and adjusted in the surgery using compressed air that is already available there.

Finally, the tray supply units illustrated in FIG. 13 also include a rinse fluid source 170 that is connected via an on-off valve 172 to the feed line 148. In this way a rinse fluid can be added to the feed line 148 even when the plungers 96, 98 have not been released, the fluid being sucked through the impression channel 18 into the connection pieces 32, 34, 36 after the tray 1 has been placed in position and secured by suction. The rinse fluid cleans the dental arch and thereby removes impurities that may damage the impression. The rinse fluid may be a rinse liquid or a rinse gas, or an aerosol. In all cases the rinse fluid may contain active constituents that have a beneficial effect on the tooth surfaces and/or the gum having regard to a good subsequent impression. Thus for example the rinse fluid may contain haemostatic agents or active constituents that reduce the secretion and/or flow of saliva.

It is understood that in a practical embodiment a plurality of rinse fluid sources may be provided, each of which is connected via an associated on-off valve to the feed line 148, in a similar way as described above for the rinse fluid source 170. These rinse fluid sources may contain different treatment materials or combinations thereof, as already mentioned in the description introduction under 4. In particular such a rinse fluid may contain a wetting agent, which is employed before producing the impression.

Instead of a rinse fluid source a warm air source may also be connected to the feed line 148 in order to dry the tooth surfaces and tissue surfaces, in which connection the air temperature may for example be between 37° and 50° C.

It is understood that with another practical embodiment exclusively rinse fluid sources may also be connected to the impression tray, and no impression material feed lines or impression material feed arrangements are used. Also, the impression tray may be used in cases not connected with producing impressions, such as treatment situations involving the administration of therapeutic agents, as already discussed in the description introduction in point 4.

After completion of the rinse phase the tray shown in FIGS. 12 and 13 is used in a manner similar to that described hereinbefore with reference to FIGS. 8 to 11.

Figure 14:
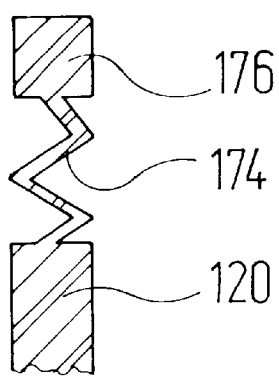
FIG. 14: Is an enlarged partial section through an edge region of a tray in which details of applying a sealing strip are reproduced.

In order to achieve a good match between the free edge of the tray edge part 118 and the geometry of a patient's mouth, that section of the edge wall 16 adjacent to the edge can be formed in a concertina-like manner, as illustrated by 174 in FIG. 14. The concertina section 174 may then carry a soft integral or attached seal 176.

Figure 15:
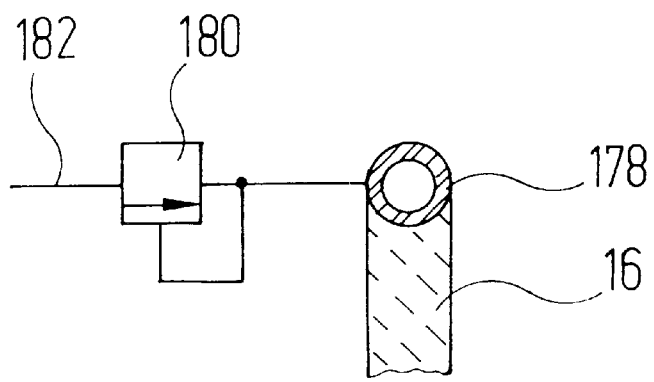
FIG. 15: Is a similar view to FIG. 14, in which a modified sealing strip arrangement is shown.

According to FIG. 15 a tube-like seal 178 that is elastically deformable may also be provided on the free edge of the edge wall 16.

As a variation of the embodiment according to FIG. 15, the seal 178 may also be formed as a flexible tube and connected via a pressure regulator 180 to a compressed air line 182, as is additionally shown in FIG. 15.

Figure 16:
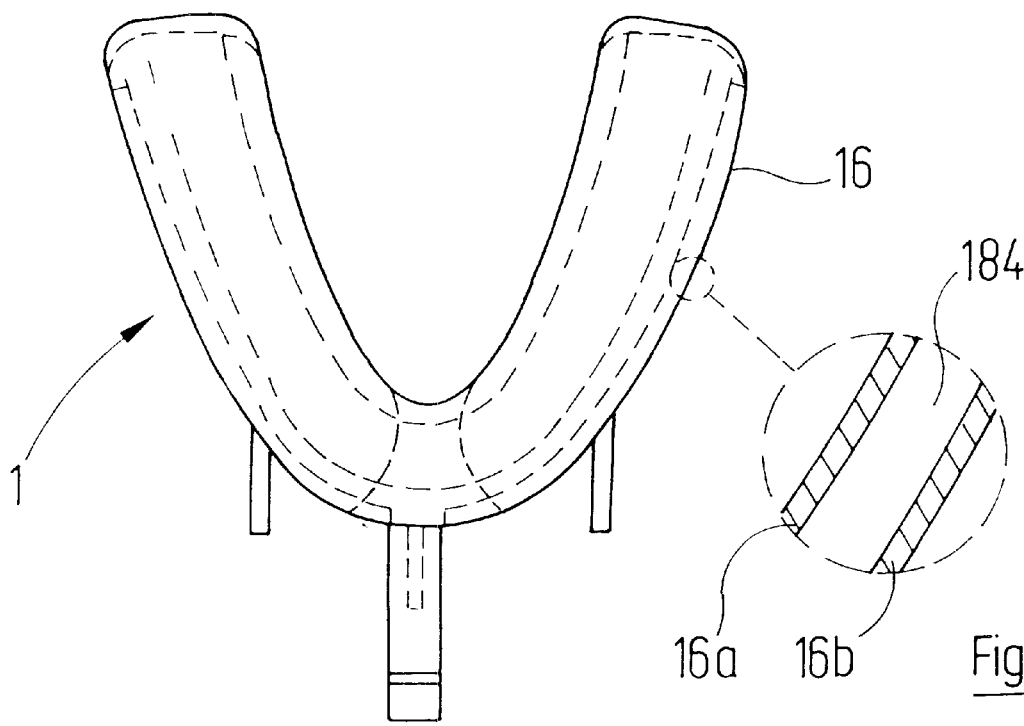
FIG. 16: Is a schematic partial section through a further modified tray, which is used in conjunction with impression materials that are heated before being introduced into the tray and that harden on cooling.

Finally, according to FIG. 16 the edge wall 16 may also be formed as a double wall consisting of individual walls 16a and 16b. The space 184 lying between the individual walls 16a and 16b is then connected to one end of the tray with a cold water feed line, and to the other end with a cold water return line. In this way preheated (temperature-controlled) impression materials can also be used in the tray, which harden under specified cooling conditions.

For the purposes of the present invention eminently suitable impression materials are in particular silicones, for example polysiloxanes, or polyethers, in each case with associated hardening, inhibiting or catalyst materials. Obviously however any other suitable impression materials may advantageously be used, for example modelling gypsum or alginates, etc.

Hydrocolloid impression materials may also be used in conjunction with the double-wall tray mould.

Figure 17:
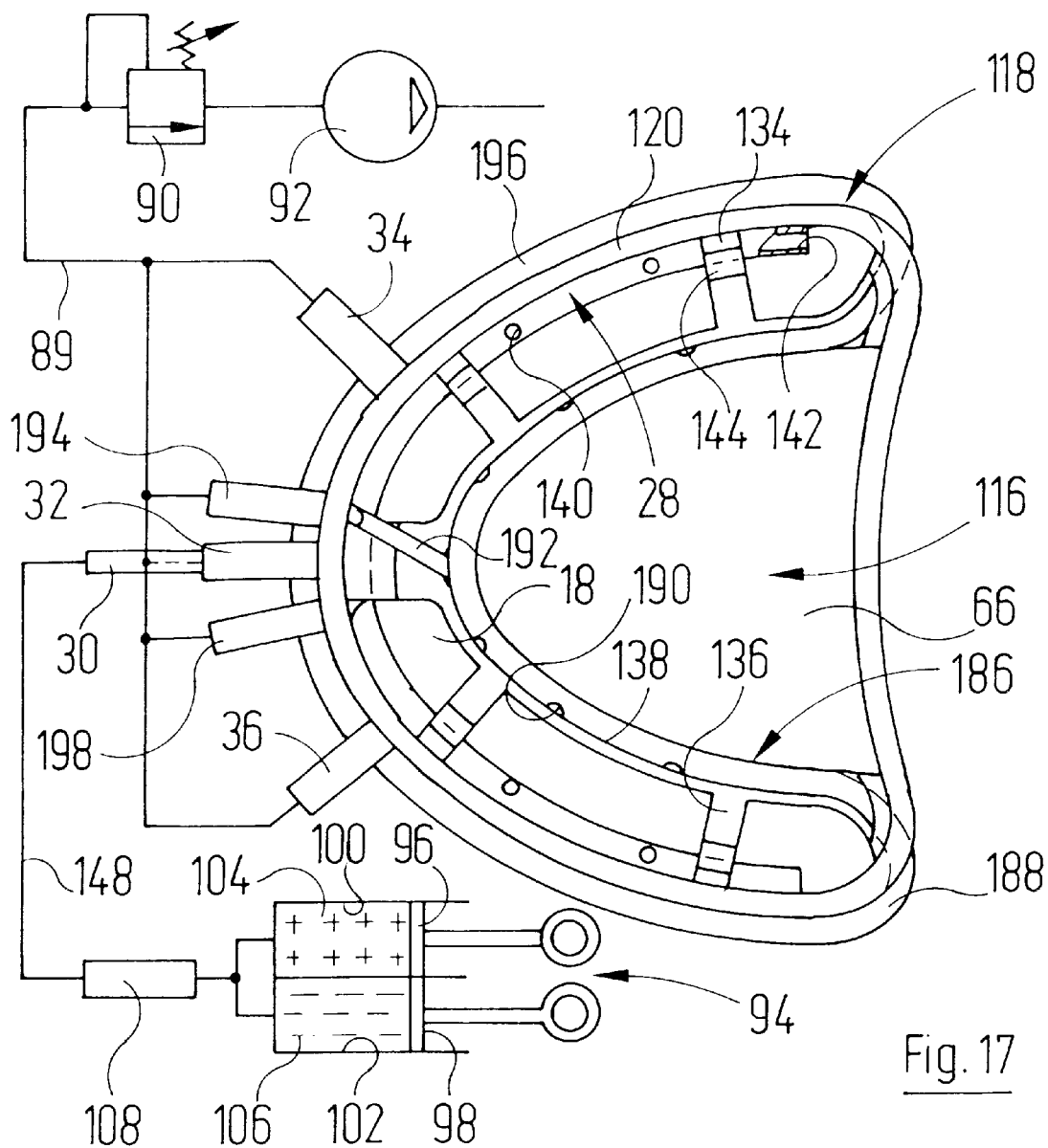
FIG. 17: Is a similar view to FIG. 9, and illustrates a further modified tray.

In the embodiment according to FIG. 17 a vacuum distributor tube 186 is provided in addition to the impression material distributor tube 28, and is likewise connected to the reduced pressure regulator 90. The distributor tube 186 has rear connection ends 188 as well at suction openings 190 formed in its wall. The suction openings 190 lie opposite the outlet openings 140. The central section of the vacuum distributor tube 186 is joined via a line 192 to a further vacuum connection piece 194 that is connected to the common reduced pressure line 89. In a similar way the connection ends 188 of the vacuum distributor tube 186 are connected to a line 196 that communicates with a further vacuum connection piece 198. The latter connection piece is in turn connected to the common reduced pressure line 89.

The impression material distributor tube 28 and the vacuum distributor tube 186 may lie in a common plane, which runs for example at the height of the neck of the tooth, but they may also be arranged at different heights, one of the distributor tubes lying at the height of the neck of the tooth while the other distributor tube lies at the height of the central cusp tips or at the height of the masticatory surfaces or incisal edges, so that an inclined rising or inclined falling flow pathway of the impression material is formed in the intersection plane perpendicular to the longitudinal extension of the impression space.

In particular the outlet openings 140 and suction opening is 190 may in each case be associated with a tooth position or a plurality of tooth positions.

It is understood that, as a variation of the embodiment according to FIG. 17, the position of the impression material distributor tube 28 and of the vacuum distributor tube 186 may be interchanged. The impression material then flows radially from the inside to the outside instead of, as in the case of the embodiment according to FIG. 17, from the outside to the inside. This shows that the feed and removal of material can be interchanged as regards position.

The position of the outlet openings 140 and of the suction openings 190 may also be chosen so that they are aligned with interdental spaces. The adjustment angle of the axes of the outlet opening 140 and of the suction openings 190 may also be changed, for example may be chosen so as to be inclined upwardly with respect to the dentition.

In order to be able simultaneously to superimpose a material flow from the rear to the front and to be able if necessary to omit the vacuum connection pieces 32, 34, 36, the outlet openings 140 and the suction openings 190 may be designed having, diameters increasing from the rear to the front. As a variation of this the central vacuum connection piece 32 may also be retained in order to maintain a vacuum in the impression space until the completion of the filling of the latter and to suck out liquids therefrom.

Figure 18:
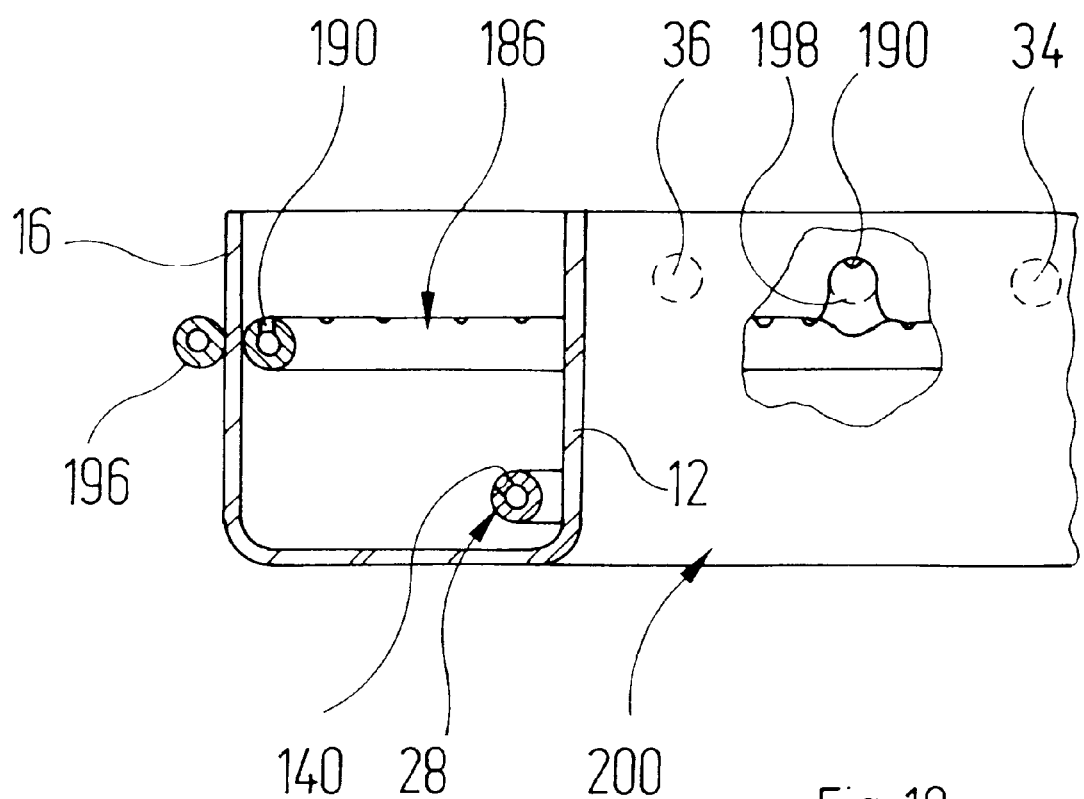
FIG. 18: Is a transverse partial section through a further modified tray.

In the embodiment according to FIG. 18 there is provided a one-piece tray main part 200 of for example flexible transparent plastics material, which seen in plan view is substantially U-shaped or V-shaped and has a substantially rectangular U-shaped transverse cross-section.

The external edge wall 16 carries, tightly clipped on, the vacuum distributor tube 186 (including the connection end 188, line 182 as well as connection elements 194 and 198). The internal edge wall 12 carries, tightly clipped on, the impression material distributor tube 28 (including the connection element 30). In this way the tubes, from which it is difficult to remove impression material that has flowed therethrough or penetrated therein, together with the impression can easily be separated from the tray main part 200.

The vacuum distributor tube 28 is arranged in the vicinity of the floor of the impression channel, and the vacuum distributor tube 186 is arranged at the height of the neck of the tooth. The vacuum suction openings 190 point upwardly, while the impression material outlet openings 140 are inclined upwardly. In this way a filling of the impression space with impression material is achieved, in which the front of the material flows on the one hand from the rear to the front, and on the other hand from below upwardly and at the same time from the inside to the outside.

The size and/or the interspacing of the impression material outlet openings 140 and/or of the vacuum suction openings 190 may vary in the longitudinal direction of the distributor tubes, in order to permit a controlled addition of the impression material, and in particular to guide the front of the impression material so that it runs to a vacuum suction opening that remains open right up to the end or to an optionally provided vacuum connection element that likewise remains open right up to the end. With the afore-described geometry the diameter may for this purpose decrease from the rear to the front while maintaining a constant interspacing of the arranged impression material outlet openings and vacuum suction openings.

In the embodiment according to FIG. 18 the vacuum connection elements 32, 34, 36 have been omitted since the vacuum distributor tube 186 is provided right up to the front section with suction openings 190.

The impression tray shown in FIGS. 19 to 23 comprises a tray base part 210 and a distributor part 212 clipped onto the latter. The tray base part is made of metal and substantially corresponds to a known impression tray, which in the conventional impression producing technique is normally filled with a kneadable impression material by the dentist and is then placed in position on an upper jaw of which an impression is to be made. The distributor part 212 is a plastics moulding.

The tray base part 210 has a curved external wall 214 and a floor wall 216. From the floor wall 216 a wall section 218 is pressed upwardly in the direction of the patient's soft palate.

The upper edge of the external wall 214 carries a beading 220 which may for example be a soldered-on wire. A beading 222 is likewise provided on the rear edge of the tray base part 210. A wire 224 is soldered onto the wall section 218 and runs parallel to the edge of the wall section 218. The wire serves to define recesses with which the impression material can interlock after it has solidified.

In addition to these known features the tray base part 210 has at least in the anterior section of the floor wall 216 a transparent window 226.

Figure 21:
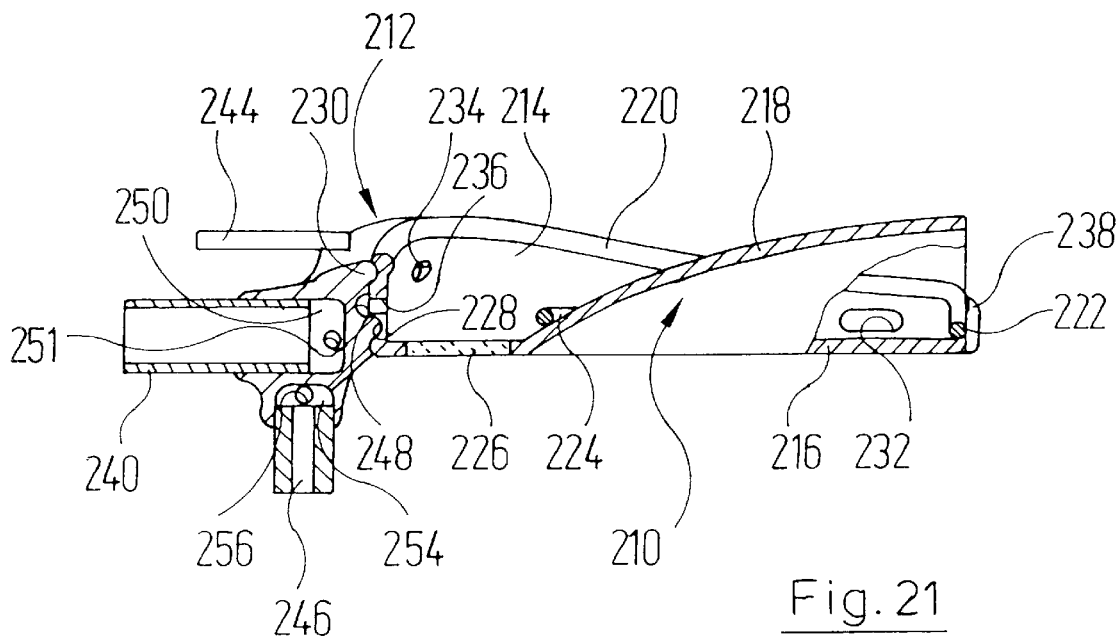
FIG. 21: Is a longitudinal section through the impression tray illustrated in FIGS. 19 and 20.

Positioning grooves 228 are formed on the outside of the external wall 214 (see FIG. 21). These grooves cooperate with complementary positioning ribs 230 that are provided on the inner surface of the distributor part 212.

Two impression material feed openings 232 are provided in the distal end section in the two arms of the external wall 214. In the anterior end section the external wall 214 has two lateral vacuum feed openings 234 as well as a central vacuum feed opening 236.

The internal surface of the distributor part 212 is exactly complementary to the external surface of the external wall 214, with the result that the distributor part 212 sits tightly and without any play on the tray base part 210. The positional relationship between the tray base part 210 and distributor part 212 can be uniquely predetermined by the positioning grooves 228 and the positioning ribs 230. The distributor part 212 has at the distal ends of its two arms in each case a catch section 238 that engages the adjacent rear end of the external wall 214 in a snap fit.

The anterior end section of the distributor part 212 carries a centrally located impression material connection piece 240 that projects forwards, two vacuum connection pieces 242, 244 arranged symmetrically to the centre plane and likewise projecting forwardly, and a further vacuum connection piece 246 that runs downwards and is separated as regards flow from the vacuum connection pieces 242, 244.

As can be seen from FIG. 22, the vacuum connection pieces 242, 244 communicate with a distributor groove 248 that has a central, V-shaped groove section and two lateral, slightly inclined groove sections. The lowest point of the central groove section is aligned with the central vacuum feed opening 236, and the lateral external sections of the distributor groove 248 form a flow medium connection to the vacuum feed openings 234.

In that region of the distributor groove 248 lying between the vacuum connection pieces 242 and 244 and the adjacent vacuum feed opening 234, a web 249 extends over the whole groove width and is of such a length that only a narrow gap remains between the back of the web and the external surface of the tray base part 210. This gap is in particular dimensioned so that on the one hand a sufficient vacuum charging of the vacuum feed openings 234 is ensured, but that on the other hand towards the end of the filling of the impression space suctioned liquid impression material on the web 249 cannot flow past on account of the only very small thickness of the remaining gap.

The web 249 thus forms a vacuum-permeable lock for the impression material, and thereby ensures that the vacuum feed opening 236 is subjected to reduced pressure up to the end of the filling of the impression space. It is furthermore ensured that the liquid impression material does not reach the vacuum connection pieces 242, 244, which of course would have to be cleaned again at disproportionate expense and effort if the impression material were to harden in the said pieces. Solidified impression material can however easily be removed from the open distributor groove 248.

If desired, similar impression material locks may be provided in those sections of the distributor groove 248 that extend between the vacuum connection pieces 242, 244 and the vacuum feed opening 236.

The realisation of the impression material lock in the distributor groove 248 by raised webs on the floor of the distributor groove is advantageous having regard to a particularly simple manufacture of the distributor part 212. It is understood that the same effect may be achieved by inserting open-pore locking elements into the distributor groove 248.

The impression material connection piece 240 communicates with a distributor space 250 from which distributor channels 251 leave, as shown in FIG. 21. The distributor channels 251 terminate in distributor grooves 252 that are arranged in the front surface of the distributor part 212 symmetrically to the centre plane and run to the distal end of the front face of the distributor part 212, in order to form a flow medium connection to the impression material feed openings 232 located there.

The further vacuum connection piece 246 communicates with a distributor space 254 at in turn communicates via symmetrically arranged distributor channels 256 with suction pockets 258 that are likewise symmetrically provided on both sides of the centre plane of the distributor part 212, the said pockets being formed as recesses in the front surface of the distributor part 212.

Figure 23:
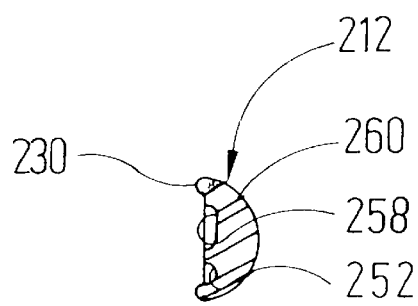
FIG. 23: Is a transverse section through the distributor part along the section line V—V of FIG. 22.

As can be seen from FIG. 23, the external surface 260 of the distributor part 212 is of spherical shape so that soft tissue can lie gently over its surface.

The impression tray is as a rule chosen to be somewhat longer in the anterior-distal direction than a conventional impression tray. The distal edge of the tray is spherical and inclined upwardly facing the palate. This is possible on account of the fact that with the impression process described here, no impression material can pass via the distal edge to the patient's throat and maybe cause vomiting or retching.

This also has the advantage that the distal end is localised in the region of the soft palate, which means that the seal is appropriately very resilient and in particular may be inclined downwardly (when attempting to blow through the held nose) and thus adapts to the distal edge of the impression tray when the latter is subjected to a vacuum, whereby the seal is maintained in the rear end of the impression tray.

The operation of the aforedescribed impression tray is described in more detail hereinafter, it being assumed that the tray base part 210 is a reusable part made of metal, whereas the distributor part 212 is a plastics disposable part in which the various connection pieces are injected or cast.

The distributor part 212 may at least on its inside be made of a permanently soft plastics material, for example of silicone. The connection pieces, which for their part may be made of metal or rigid plastics material, are injected or cast in this plastics part.

If desired a metal or rigid plastics part may also be inserted into the distributor part 212, the said metal or plastics part having a strap-like shape and serving to mechanically stabilise a distributor part 212 made of soft plastics material and also in this case permitting the distributor part to be clipped onto the tray base part 212, the embedded strap performing the clip-on function.

A new distributor part 212 is clipped onto a sterilised tray base part 210. The vacuum connection piece 246 is subjected to a vacuum. A firm interlocking of the base part to the distributor part 212 is now ensured by subjecting the suction pockets 258 to reduced pressure.

A 3–5 mm thick strip of silicone sealing compound is applied to the rear edge of the tray base part.

The silicone sealing compound is preferably a kneadable silicone (kneadable consistency) which does not harden in one stage and is deformable at the temperature of the mouth and under the pressure exerted on inserting the impression tray into the mouth. This kneadable silicone thus lies like a tough plastics strip between the impression tray and teeth as well as the soft tissues, so as to form a good sealing point. The silicone sealing compound is preferably chosen so that it combines with the impression material, thereby avoiding the formation of any gap spaces that are difficult to disinfect.

As a further alternative all the tray edges or also just the external surface of the distributor part may be individually matched before producing the impression, by building them up with a plastic and hardenable compound (for example silicone or thermoplastic material).

It is understood that scaling measures different to those outlined above may also be employed at different sections of the impression tray.

The seal produced by a deformable compound extends over the upper jaw, in particular to the region of the palate arch, in order thereby to form a channel between the sealing compound and the labial tray wall. This improves the directed flow of the impression material. In the lower jaw the region to be scaled, possibly with the additional use of sealing compound, extends to the retromolar triangle distally of the most dorsally located back teeth in the immediate vicinity of the ridge of the jaw.

In a preferred embodiment of an impression tray the impression material connection piece is first of all closed with a reusable valve or a single-use valve, for example sealed with a foil.

This enables the impression tray to be positioned and fixed under application of a vacuum and also enables the vacuum to be adjusted to a value at which the gum papillae easily retract from the tooth and the sulci easily retract peripherally, at least around the teeth of which an impression is to be made. In order to facilitate such a retraction one or more binding threads may previously be inserted in the sulci, which remain in place during the formation of the impression or may be removed beforehand.

Only when optimum conditions for the impression exist, for example it is visually checked that moderate bleeding has stopped, is the impression material source connected to the impression material connection pieces, for example to a mixing chamber of a double syringe for the binder component and the hardener component of the impression material. A sealing point is first of all produced in the connection region before the valve provided in the impression material connection piece or the sealing membrane is opened. This has the advantage that the previously set vacuum does not need to be changed and the secure positioning of the tray remains unaltered.

Alternatively the impression material, for example after activating a flexible double bag (by pressing a scam sealing point), can be premixed by intensive kneading or mechanical rolling of the material or in any other suitable way, and fed in the mixed state by manual expression by hand or motorised means to the impression material connection piece.

In order to prevent the tray working loose should the double syringe move when it is actuated or if the patient moves, the double syringe is connected via a flexible tube to the impression material connection piece.

When the impression tray is inserted into the patient's mouth the sealing compound strip is deformed according to the contours of the patient's soft palate.

The soft tissue adjacent to the upper jaw lies under tension over the external surface of the distributor part 12 and thus forms there an overall sealing point. If an accurate impression of individual regions is not important when producing an impression, then so-called stops of a deformable permanently soft and/or hardening compound, for example of a thermoplastic material or wax, may be applied to the tray wall opposite the occlusal surface of the teeth. Such stops serve to effect an even more secure positioning of the impression tray under a vacuum charging.

The impression space defined by the patient's jaw and the impression tray is, as described above, evacuated by application of a vacuum through the vacuum connection pieces 242, 244. In this way the impression tray is immovably positioned on the patient's jaw. At the same time liquid present in the impression space is sucked out from the patient's mouth. As a result of the reduced pressure the edges of the gums are also slightly retracted from the teeth. If necessary, in addition to this suctioning the impression space must be ventilated via the impression material connection piece and impression material feed opening.

If liquid impression material is now added to the impression material connection piece 240, the material flows through the distributor space 250, the distributor channels 251 and the distributor grooves 252 to the impression material feed openings 232 and enters through the latter into the rear end of the impression space. The front of the liquid impression material displaces forwardly any liquids present in the impression space in the direction of the vacuum feed openings 334 and 336. The impression material flows along the teeth in the impression material from the rear to the front and forms a sharp impression of the teeth, a sharp impression of the sections of the teeth situated there also being produced by the retraction of the gum edges.

The filling of the impression space with impression material can be visually monitored by the dentist through the window 226. When the vacuum connection pieces 242 and 244 are full of impression material, the supply of impression material can be stopped. After the impression material has hardened the impression tray is then removed from the jaw.

After the impression material has hardened the distributor part 212 is removed from the tray base part 210 and thrown away. Alternatively, the distributor part 212 may also be cleaned, disinfected, sterilized and reused.

The tray base part may be cleaned, sterilized and reused after producing the impression. An existing vacuum source or an extra venturi nozzle provided for this purpose and operated with compressed air may be used to produce a vacuum in the vacuum connection pieces 242, 244 as well as in the vacuum connection piece 246 independent of the latter as regards flow.

The invention has been described hereinbefore on the basis of an impression tray for the upper jaw; it is understood of course that it can also be used, with suitable modifications, for lower jaw impression trays.

Obviously such an impression tray can also be used only to produce impressions of parts of the jaw, for example one half of the jaw or jaw segments. If an impression of only one half of the jaw is to be produced, the impression material feed opening of the tray base part is closed for example by a matching ready-made stop or by a plastic or initially plastic and then hardening substance, or alternatively the impression material distributor groove of the tray distributor part of the side not corresponding to the impression is closed. Alternatively regions not involved in forming the impression may be excluded from the impression process by prior insertion and positioning of preferably plastically deformable dead space bodies, for example foam, kneading compounds, cotton wool plugs, etc. at the corresponding place before adjusting and filling the tray, which results in a substantial saving in material.

Figure 19:
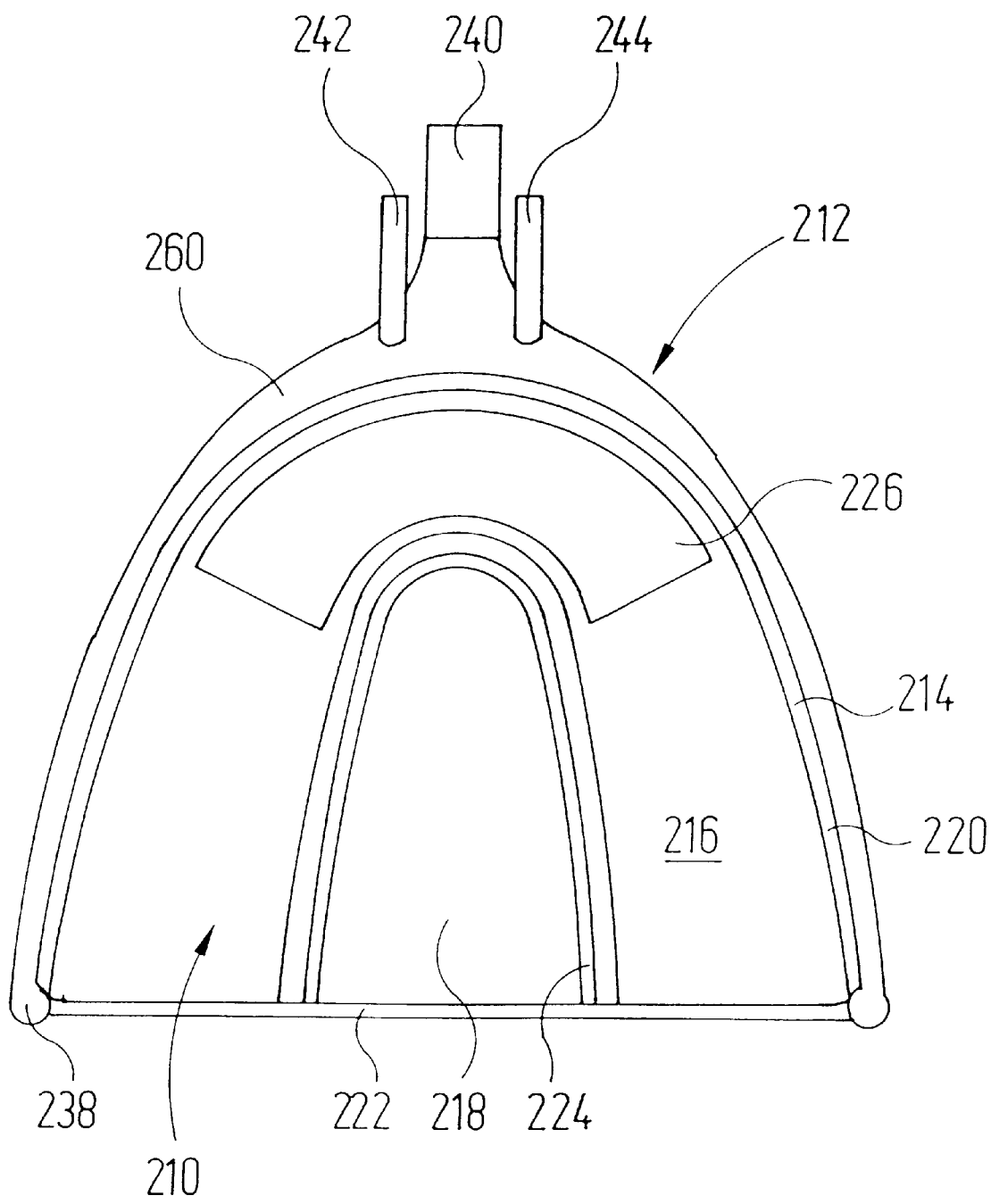
FIG. 19: Is a plan view of the upper side, facing the teeth, of a further upper jaw impression tray according to the present invention.
Figure 20:
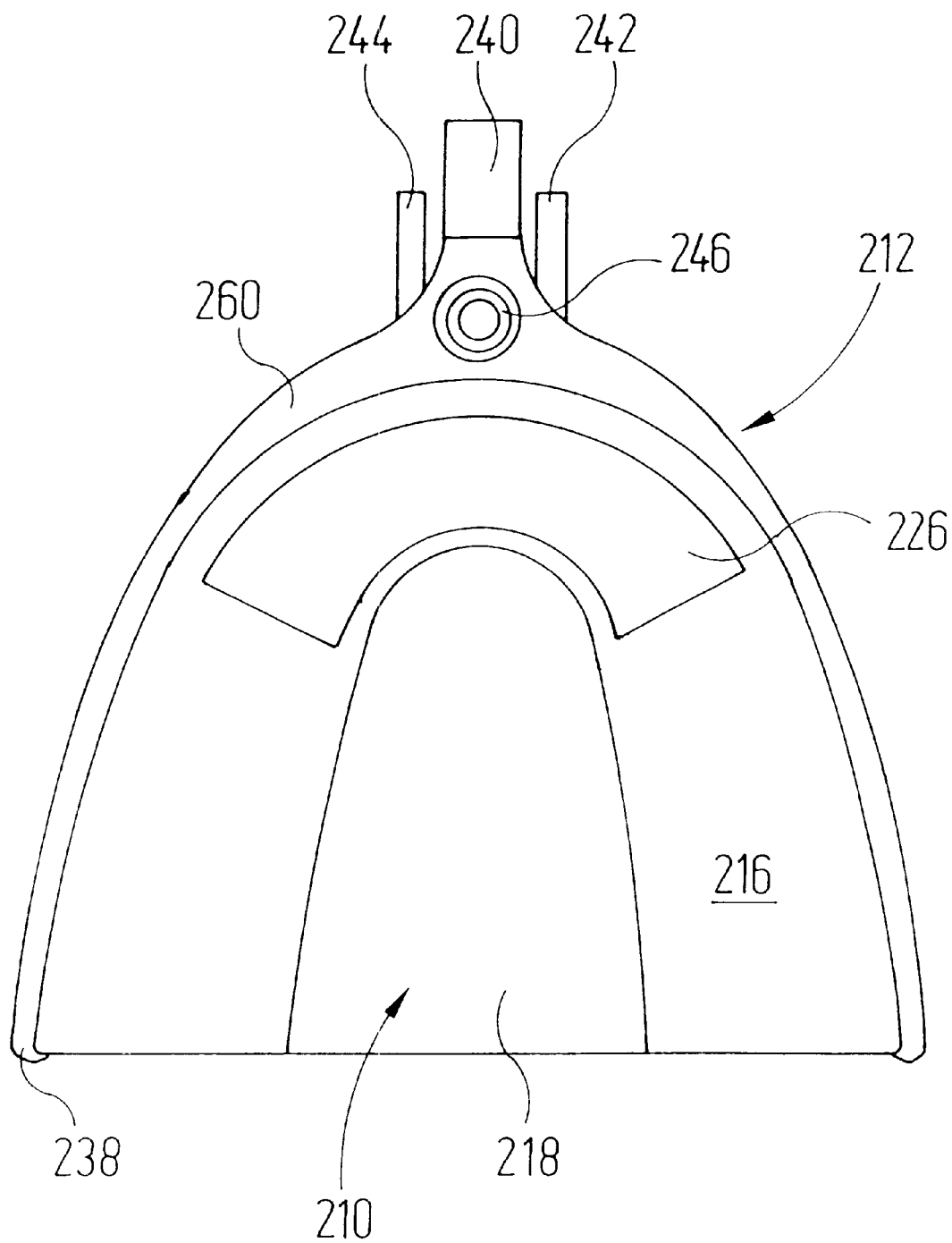
FIG. 20: Is a plan view of the underneath of the impression tray illustrated in FIG. 19.
Figure 24:
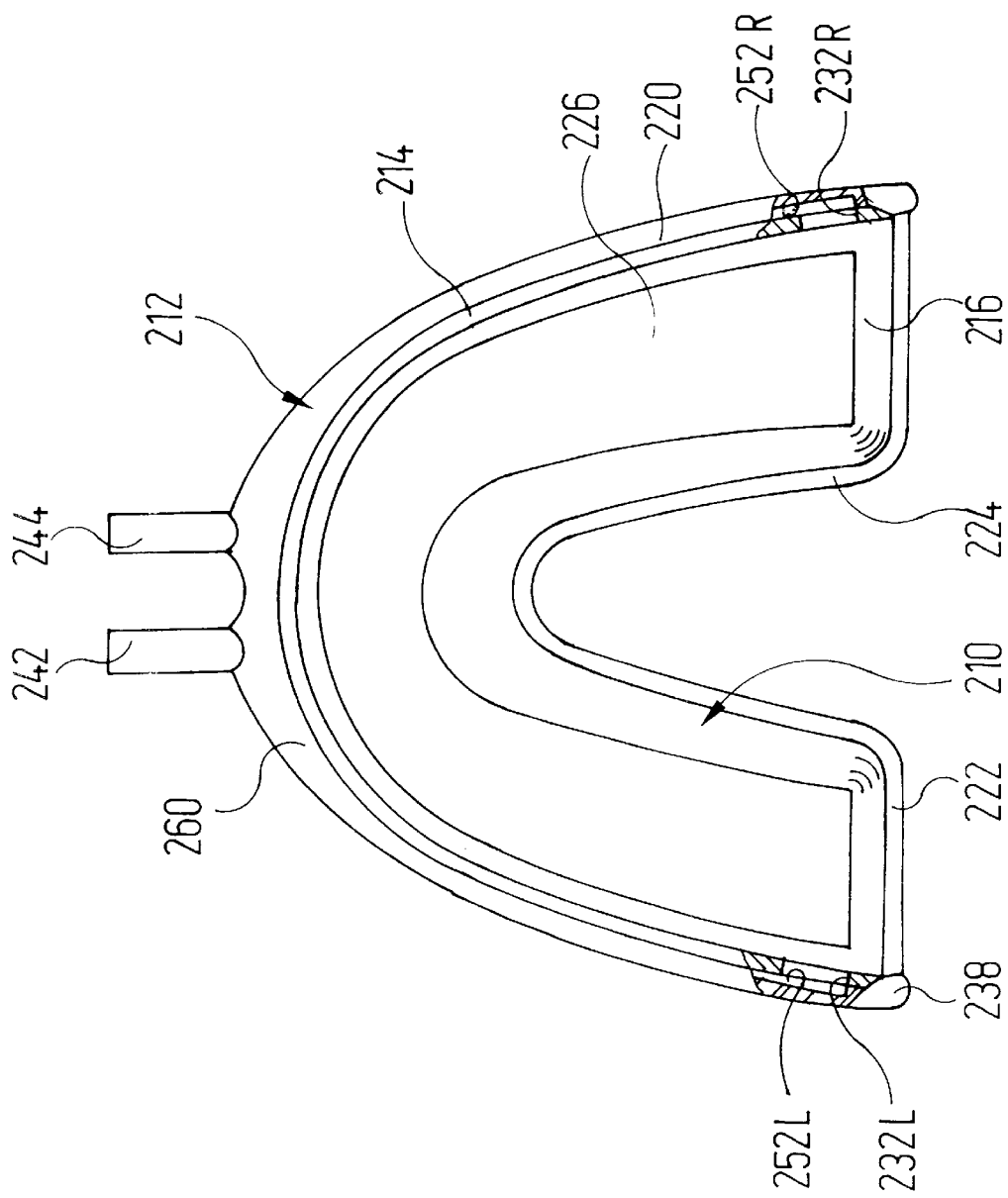
FIG. 24: Is a plan view of the underneath side under conditions of use of a further modified tray for producing a lower jaw impression.
Figure 25:
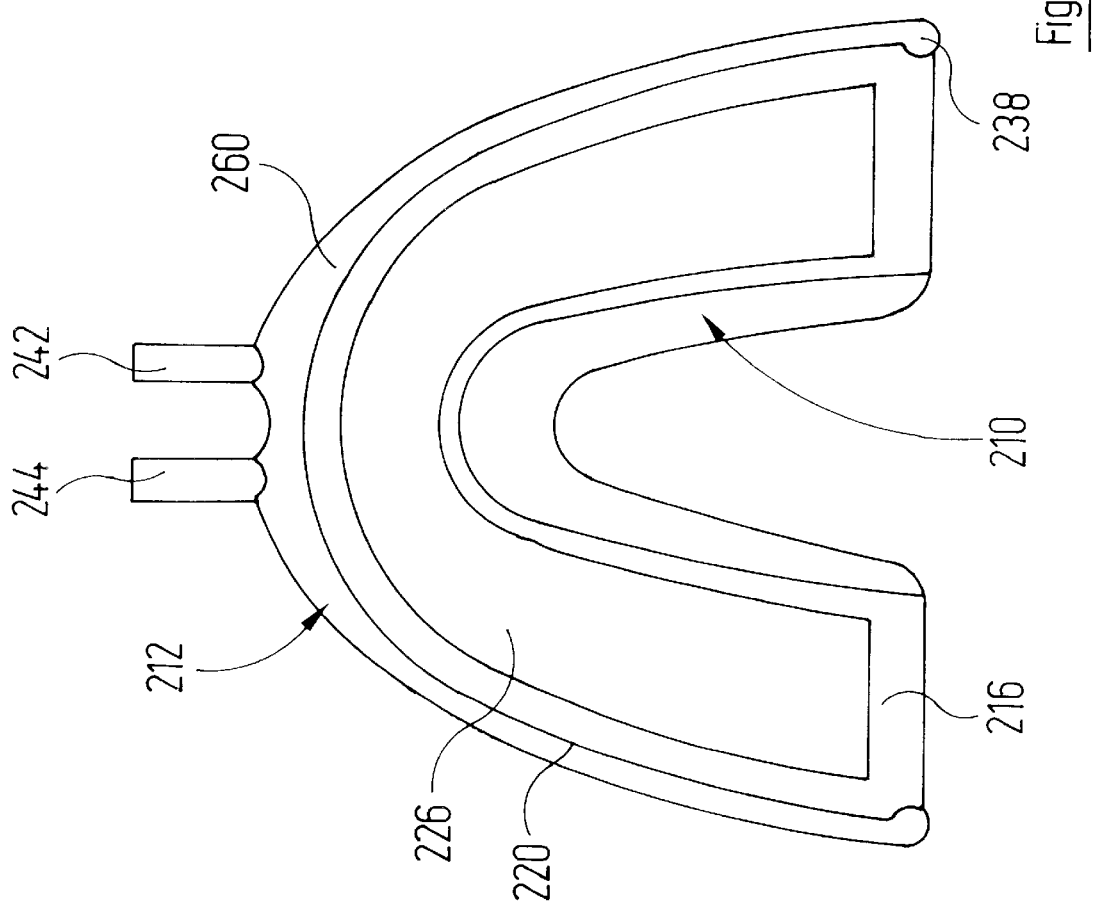
FIG. 25: Is a plan view of the upper side under conditions of use of the tray according to FIG. 24.
Figure 26:
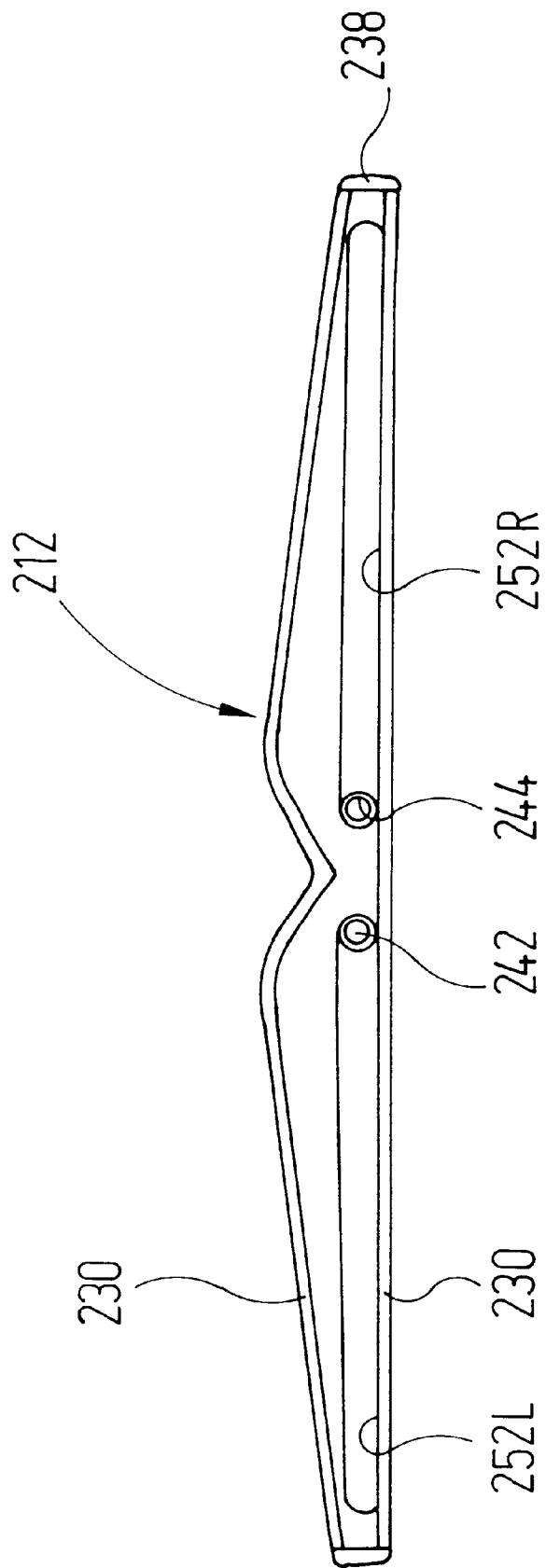
FIG. 26: Is a developed plan view of the interior surface of a distributor part tray according to FIGS. 24 and 25 on a reduced scale.

The tray illustrated in FIGS. 24 to 26 is, as regards its two-part basic construction, very similar to the tray illustrated in FIGS. 19 and 20. Components corresponding to functionally already described components are again provided with the same reference numerals (as per the description of the figures) and are therefore not described again in detail. Where a distinction has to be made between constituents lying on both sides of the plane of symmetry, this is effected by the additional letters "R" (for right-hand) and "L" (for left-hand).

The tray shown in FIG. 24 is intended to produce impressions of a patient's lower jaw and its window 226 extends over the whole floor wall 216 of the tray base part 210.

The distributor part 212 carries only two connection pieces 242, 244, which depending on the specific use may serve as vacuum connection pieces or impression material connection pieces.

If in use the connection piece 244 for example is connected to the vacuum source and the connection piece 242 is connected to the impression material source, then the tray in FIG. 24 fills from the left from the bottom upwards and then to the right downwards. The progress of the front of the impression material can easily be observed through the window 226. The filling of the impression space can be terminated at any time by visually checking when a relevant part of the jaw has been surrounded by impression material. The tray according to FIGS. 24 to 26 is thus particularly suitable for producing partial impressions.

Figure 27:
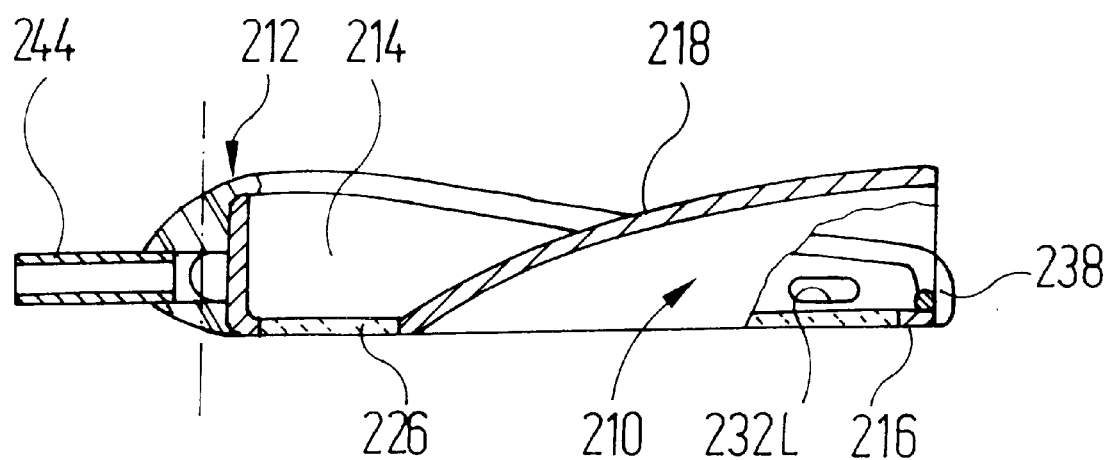
FIG. 27: Is a longitudinal section through a modified tray for producing an upper jaw impression, that part of the tray furthest to the left being shown in a displaced passing through one of the connection pieces of the tray.

FIG. 27 shows a corresponding tray that is intended for use on the upper jaw.

Figure 28:
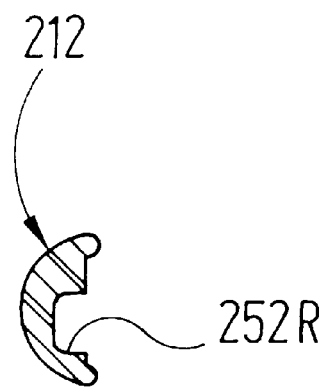
FIG. 28: Is a transverse section through a distributor part of the tray according to FIG. 27.

FIG. 28 shows a transverse section through one of the arms of the distributor part 212.

The trays described in detail above may also be designed for producing negatives of tooth models instead of producing jaw impressions, which in turn have been produced by the casting of jaw impressions. The trays are then used together with a cavity mould on which a tooth model is positioned and which in addition simulates the function of the soft tissues in the mouth, in order to define together with the tray a tight impression space.

Figure 29:
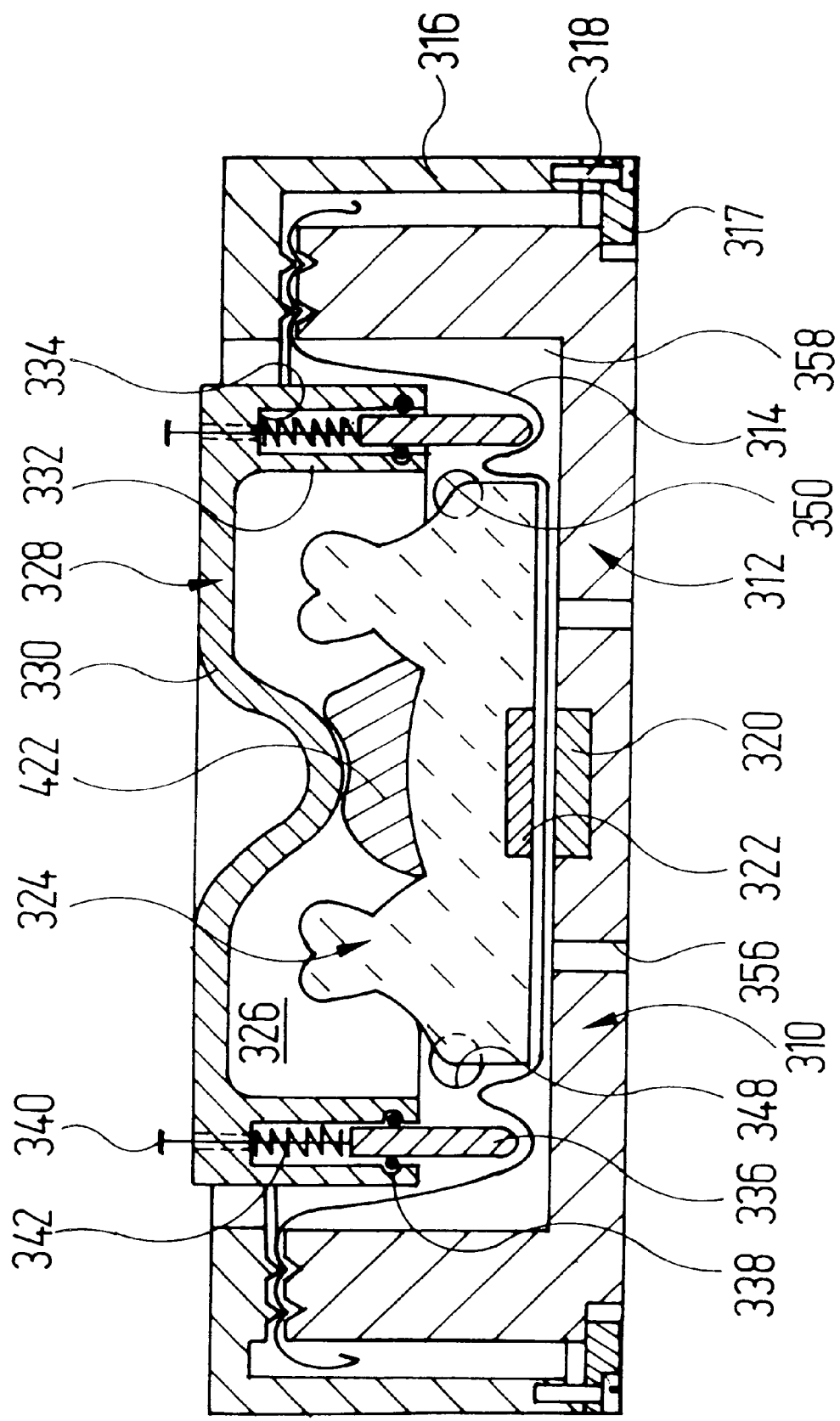
FIG. 29: Is a transverse section through a further modified tray that is used for copying tooth models, together with a cavity mould that in conjunction with the tray defines a tight hollow space that surrounds the tooth model.

A corresponding cavity mould is denoted overall by the reference numeral 310 in FIG. 29. It has a bowl-shaped, upwardly open housing 312 on whose upper edge is secured an elastic impression space membrane 314. This membrane runs in the unstressed state substantially horizontally over the housing 312.

The edge of the impression space membrane 314 is joined to the front face of the peripheral wall of the housing 312 by a cylindrical clamping frame 316. A clamping ring 317 is located on the lower edge of the frame. Clamping screws 318 that run in threaded bores provided on the lower end of the clamping frame and whose heads engage on the clamping ring 317 serve to fasten the clamping ring 317 and the clamping frame 316 to the housing 312.

A magnet 320 is accommodated in the floor of the housing 312. This magnet cooperates with a magnet 312 (or a plate of magnetic material such as iron) that is housed in the underneath of a tooth model 324. The tooth model 324 is produced in a conventional way by casting a tooth impression, for example with gypsum.

If a tray is mounted on the impression space membrane 314 so that the free edge of the peripheral wall of the tray additionally tensions the impression space membrane 314, then the tray together with the impression space membrane 314 defines an impression space 326 similar to that produced by one of the aforedescribed trays together with the soft tissues adjacent to the dentition of a patient's mouth.

FIG. 29 shows a modified tray 328 instead of one of the aforedescribed trays, this modified tray being particularly suitable for copying purposes since it enables the size of the impression space 326 to be varied according to the height of the tooth model 324, thereby saving impression material.

The tray 328 has a floor part 330 and a stationary wall part 332 carried by the edge of the floor part. The wall part is provided with a groove 334 running in the longitudinal direction of the wall, in which groove engages a wall part 336 movable in the vertical direction in FIG. 29. The sides of the wall part 336 are sealed against the groove 334 by seals 338. A plurality of stop screws 340 distributed in the longitudinal direction of the groove engage on the upper-lying front face of the movable wall part 336, the said screws running in a vertically adjustable manner in threads provided in the edge region of the floor part 330. The stop screws 340 are each surrounded by a helical spring 342, whereby the movable wall parts 336 are prestressed in an extended position.

Figure 30:
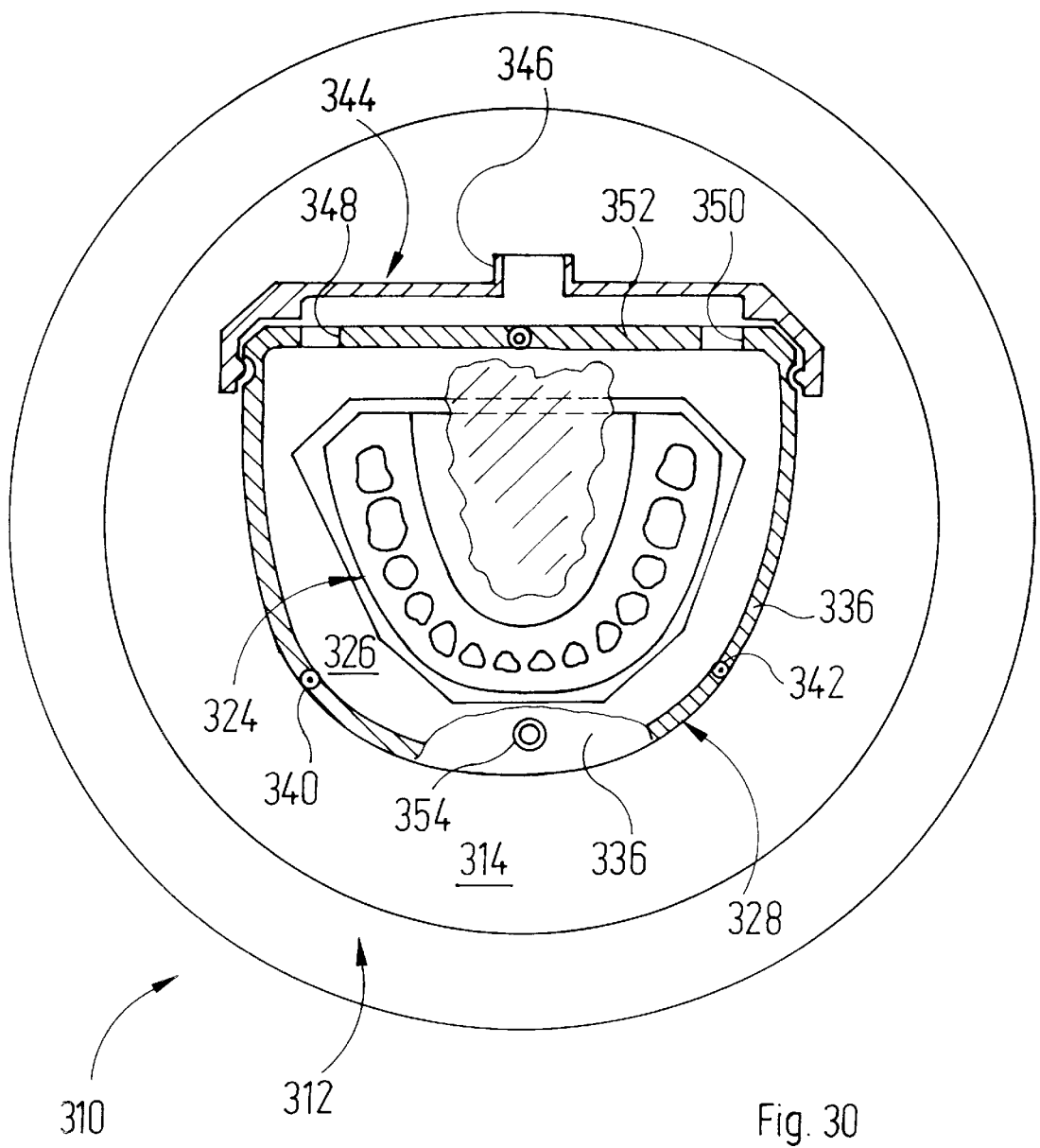
FIG. 30: Is a horizontal section through the copying device illustrated in FIG. 29.

As can be seen from FIGS. 29 and 30, the tray 328 has a distributor part 344 mounted on its rear side with an impression material connection piece 346. Impression material is conveyed through the distributor part 344 to feed openings 348, 350 provided in a rear wall 352 of the tray 328. A connection piece 354 for making a connection to a reduced pressure source may be provided in the front, under operating conditions the upper, section of the floor part 330, as illustrated in FIG. 30.

The addition of impression material to the connection piece 346 may be effected in a similar way as described hereinbefore in connection with producing intraoral impressions. The same comments apply as regards the reduced pressure charging of the connection piece 354, with the proviso that when setting the strength of the vacuum attention need not be paid to damage to vital tissues. A strong vacuum (pressure reduction) down to 990 mbar below normal pressure may thus also be set. This makes it possible to suck in the impression material only under vacuum and to operate without additionally subjecting the fed-in impression material to pressure.

If the tray 328 is operated without being subjected to a vacuum, then the pressure of the added impression material can also be chosen to be greater than when making intraoral impressions, since in this case too attention does not have to be paid to possible tissue damage. If the tray 328 is placed in a suitable manner against the impression space membrane 314 (for example by clamping screws engaging in FIG. 29 on the upper side of the tray 328), then feed pressures of up to 15 bar may be used for the impression material. This also enables the addition of impression material to be effected exclusively by subjecting the latter to high pressure, and to avoid having to evacuate the impression space. In this case the vacuum feed openings then serve to ventilate the impression space.

Since also in the case of the copying arrangement according to FIGS. 29 and 30 the material flows around the teeth (tooth model) instead of the teeth being pressed into a plastically deformable material, the same advantages as described hereinbefore are again obtained.

As can be seen from FIG. 29, bores 356 are provided in the floor of the bowl-shaped housing 312. The membrane back space 358 between the impression space membrane 314 and the housing floor is ventilated via these bores. In one variant the bores 356 can also be connected to an adjustable, low reduced pressure source, in order already to produce a pre-shaping of the impression space membrane to achieve a substantially dome-shaped configuration. The edge of the tray 328 then no longer needs to deform the impression space membrane so strongly.

Figure 31:
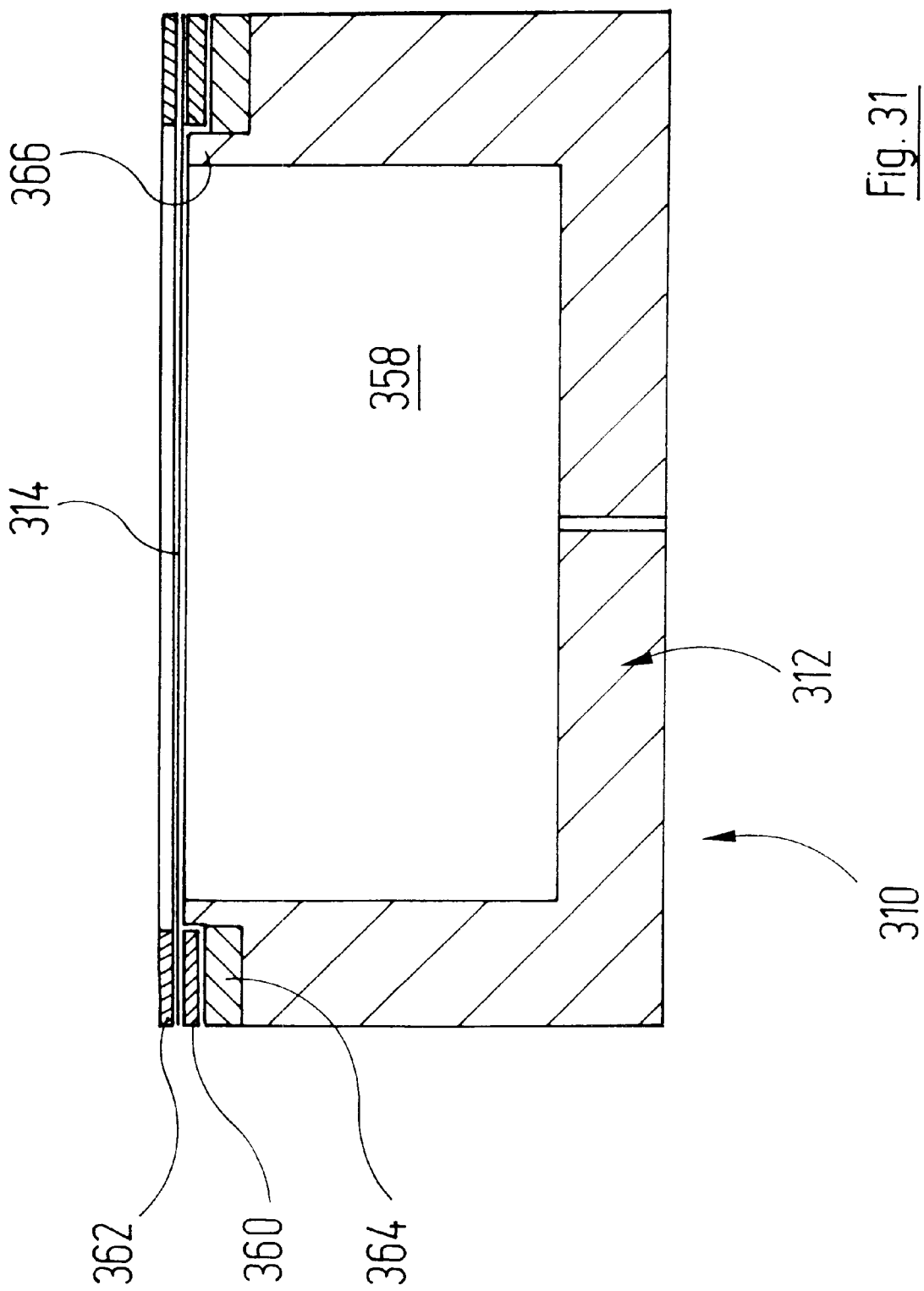
FIGS. 31 to 33: are transverse sections through modified cavity moulds which together with a tray can form a copying device.

FIG. 31 shows another way of securing the impression space membrane 314 on the housing 312. The edges of the impression space membrane 314 are clamped between rings 360, 362 made of iron, and an elongated permanent magnet 364 (or a series of smaller permanent magnets) is accommodated in the upper side of the circumferential wall of the housing 312. As can be seen from FIG. 31, a rib section 366 of the circumferential wall of the housing 312 projects upwardly over the front face of the permanent magnet 364 and thus forms a radial stop means for the lower ring 362. In this way the impression space membrane 314 can also be strongly loaded without the risk of its edge coming lose.

Figure 32:
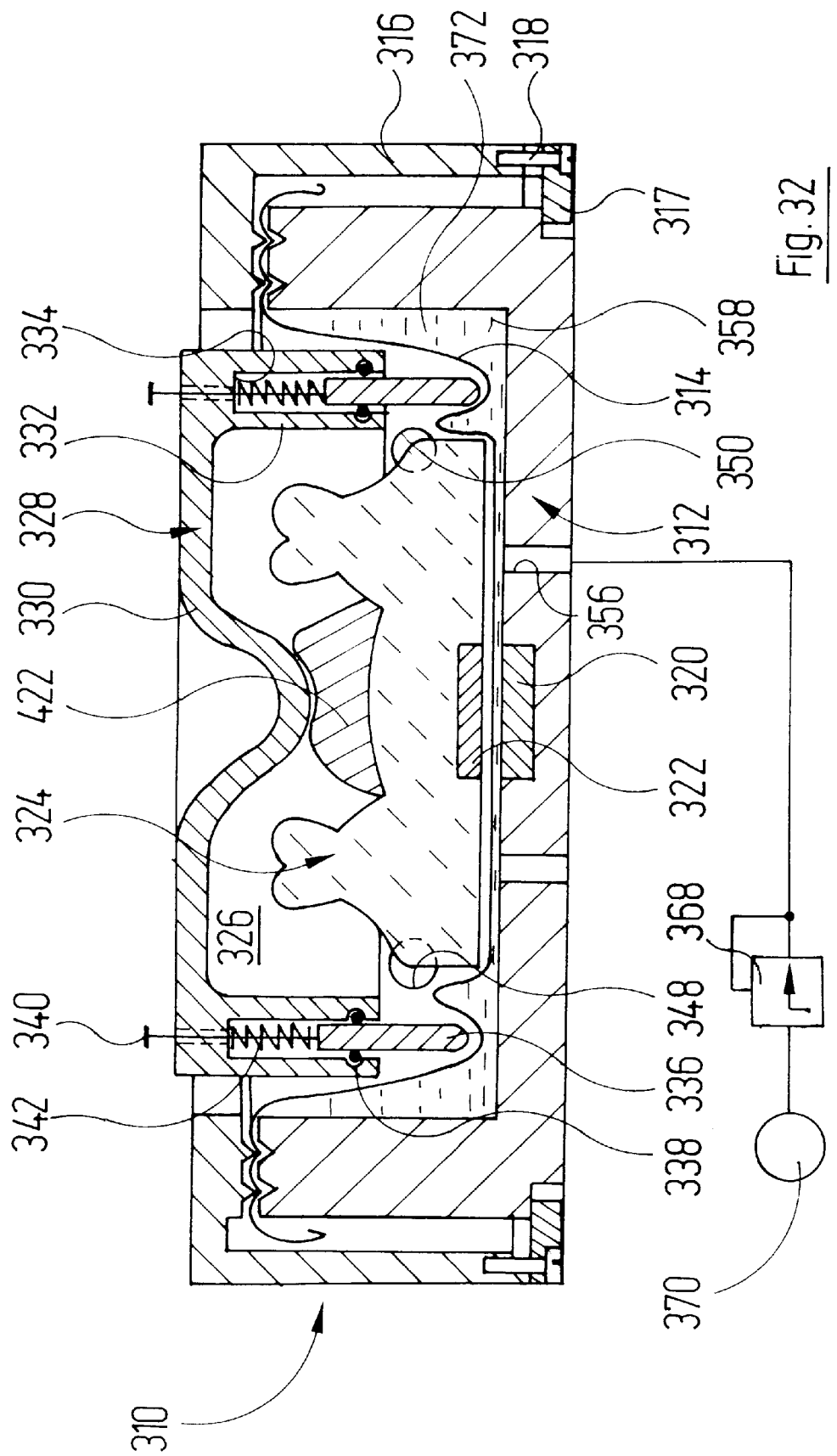

The cavity mould 310 shown in FIG. 32 corresponds in its basic mechanical construction to that according to FIGS. 29 and 30. In the floor of the housing 312 only a single bore 356 is now provided however, and this communicates via a pressure regulator 368 with a pressure medium source 370. The fluid released from the pressure source 370 is preferably a liquid or a gel. A cushion 372 of liquid or gel is thus formed underneath the impression space membrane 314.

Figure 33:
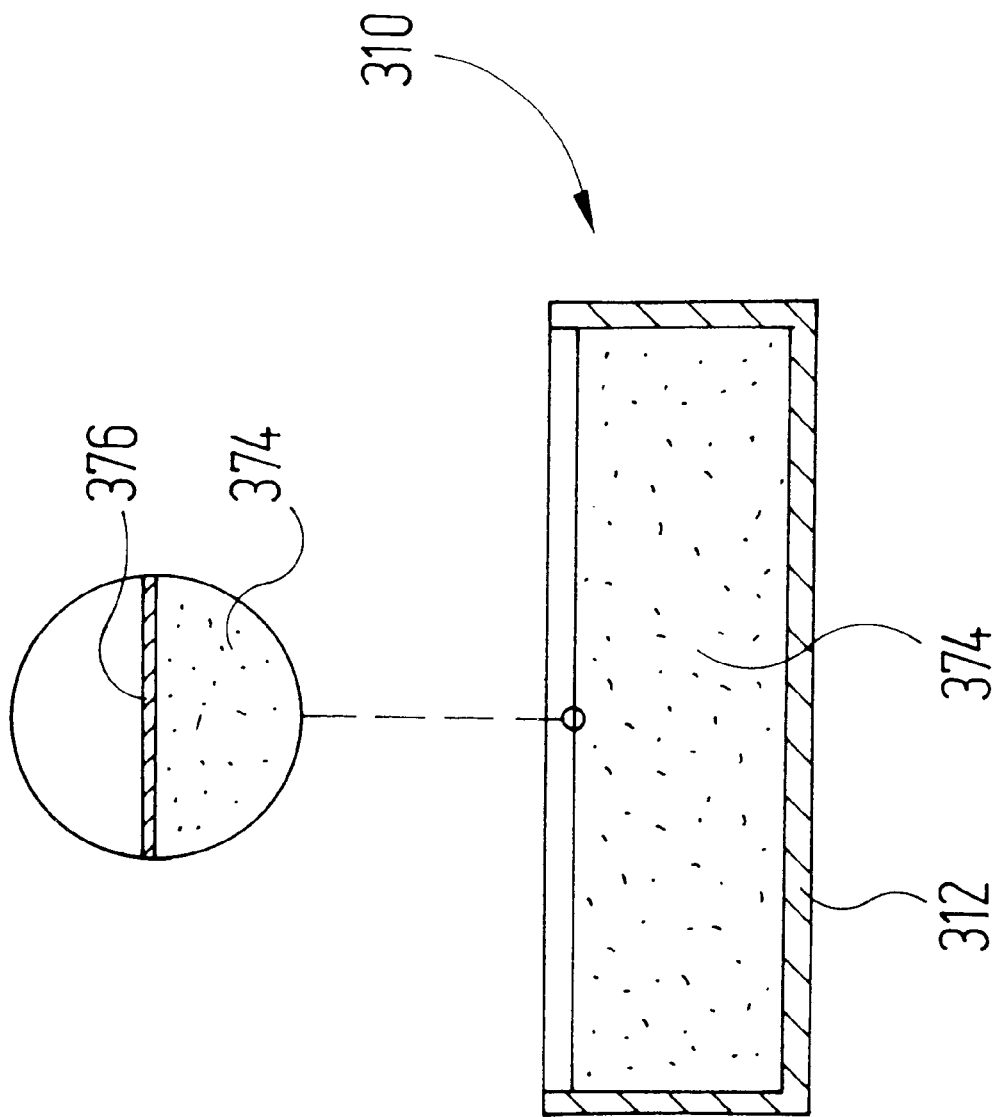

In the case of the cavity mould 310 shown in FIG. 33 a flexible foam part 374 is inserted into the bowl-shaped housing 312. As is evident from the enlarged section, this foam part has a surface skin 376 produced during foaming that is impermeable to flow medium. Alternatively, a film impermeable to flow medium and which replaces the surface skin 376 may be placed on the upper side of an open-pore foam part.

Figure 34:
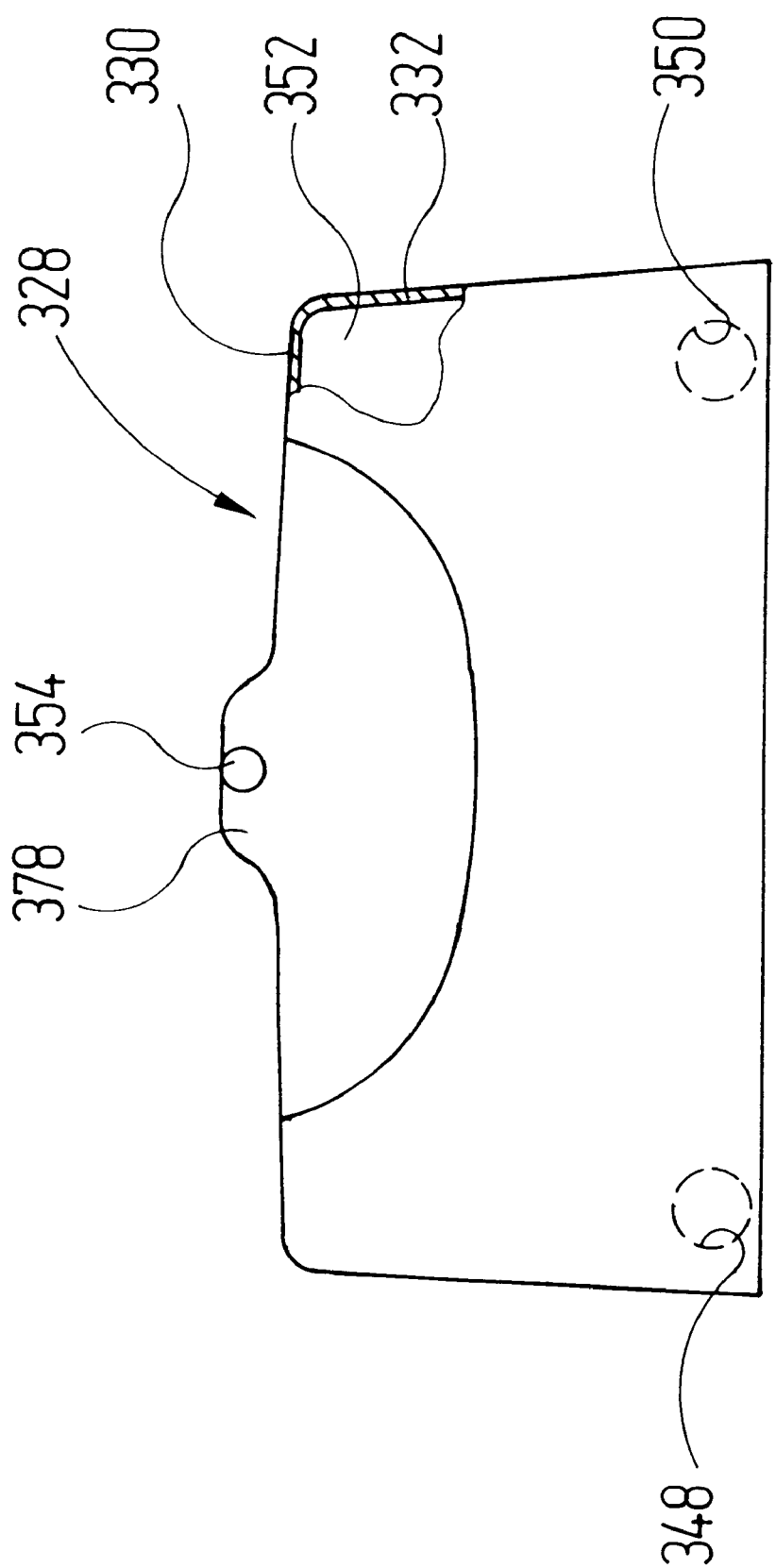
FIG. 34: Is a plan view of the rear side of a simple tray for copying purposes.

FIG. 34 shows a modified tray 1 that corresponds as regards the flow conditions to the tray shown in FIG. 29, except that it is formed as a vacuum deep-drawn disposable part. The vacuum connection piece 354 is provided in a raised section 378 of the floor part 330.

Figures 35, 36:
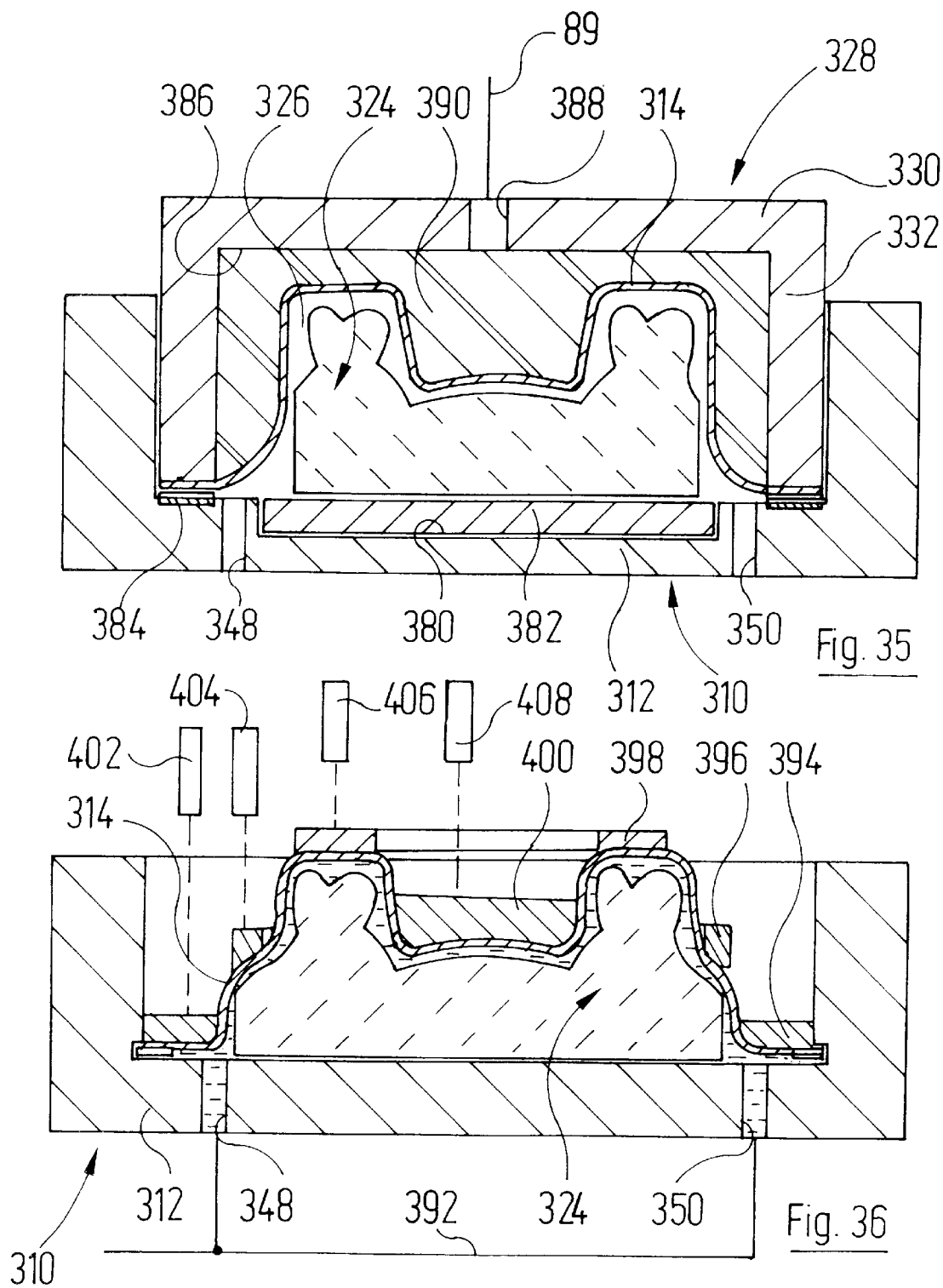
FIG. 35: Is a transverse section through a further modified copying device, in which the tray has a deformable impression space membrane.
FIGS. 36 and 37: are similar views to FIG. 35, in which further modified copying devices are reproduced.

In the copying arrangement shown in FIG. 35 the floor of the housing 312 is provided with a recess 380 in which a model base plate 382, which in turn carries the tooth model 324, can be inserted in a positively engaging manner. The impression space membrane 314 is now mounted at the end of the circumferential wall of the bowl-shaped tray 328. In its region lying underneath the circumferential wall of the tray 328 a seal 384 is inserted into the floor of the housing 312.

The impression space membrane 314 now defines together with the bowl-shaped housing of the tray 328 a working space 386 that is accessible via a bore 388 in the upper-lying wall of the tray 328.

In order to set an accurately predetermined spacing, between the impression space membrane 314 and the tooth model 324 when producing the tooth impression, a supporting body 390 is inserted into the working space 386, the downwardly pointing front face of the supporting body being contoured according to the geometry of the impression space membrane when producing the impression. The supporting body 390 is made of an air-permeable material, for example open-pore foam material or a loose metal felt, and by subjecting the working space 386 to a reduced pressure that is greater than the reduced pressure in the impression space 326, it is ensured that the impression space membrane 340 lies against the front face of the supporting body 390.

In the copying device according to FIG. 36 the size of the impression space 326 dynamically adjusts under the forces acting on the impression space membrane 314

The underneath of the impression space membrane 314 tightly secured on the lower end of the circumferential wall of the housing 312 is subjected to the pressure of the impression material added through a feed line 392. Weights associated with various surface regions of the impression space membrane act downwardly: a weight 394 associated with the external edge of the impression space membrane, a weight 396 associated with the transitional region between the jaw and teeth, a weight 398 associated with the tooth surfaces, and a weight 400 associated with the central model region.

The weights match as regards their basic geometry the standard geometries of the various model sections. Since the weights are in any case raised during the production of the impression of the tooth model, a better matching to the geometry of the model that is about to be formed is not necessary.

By choosing materials of different densities (for example plastics/aluminium/iron) it can be determined in advance which weights are raised more and which less when the impression material is fed in. In this way the thickness of the impression material layer can be locally regulated.

Also, the geometry of the weights has an effect on the local thickness of the model impression.

Optical position indicators 402 to 408 are arranged above the weights 394 to 400, which measure the rise of the weights caused by feeding in impression material under the impression space membrane 314. The existence of a sufficiently thick layer of impression material over the tooth module 324 can be detected on the basis of the output signals from the position indicators 402 to 408. The addition of further impression material is then stopped.

Figure 37:
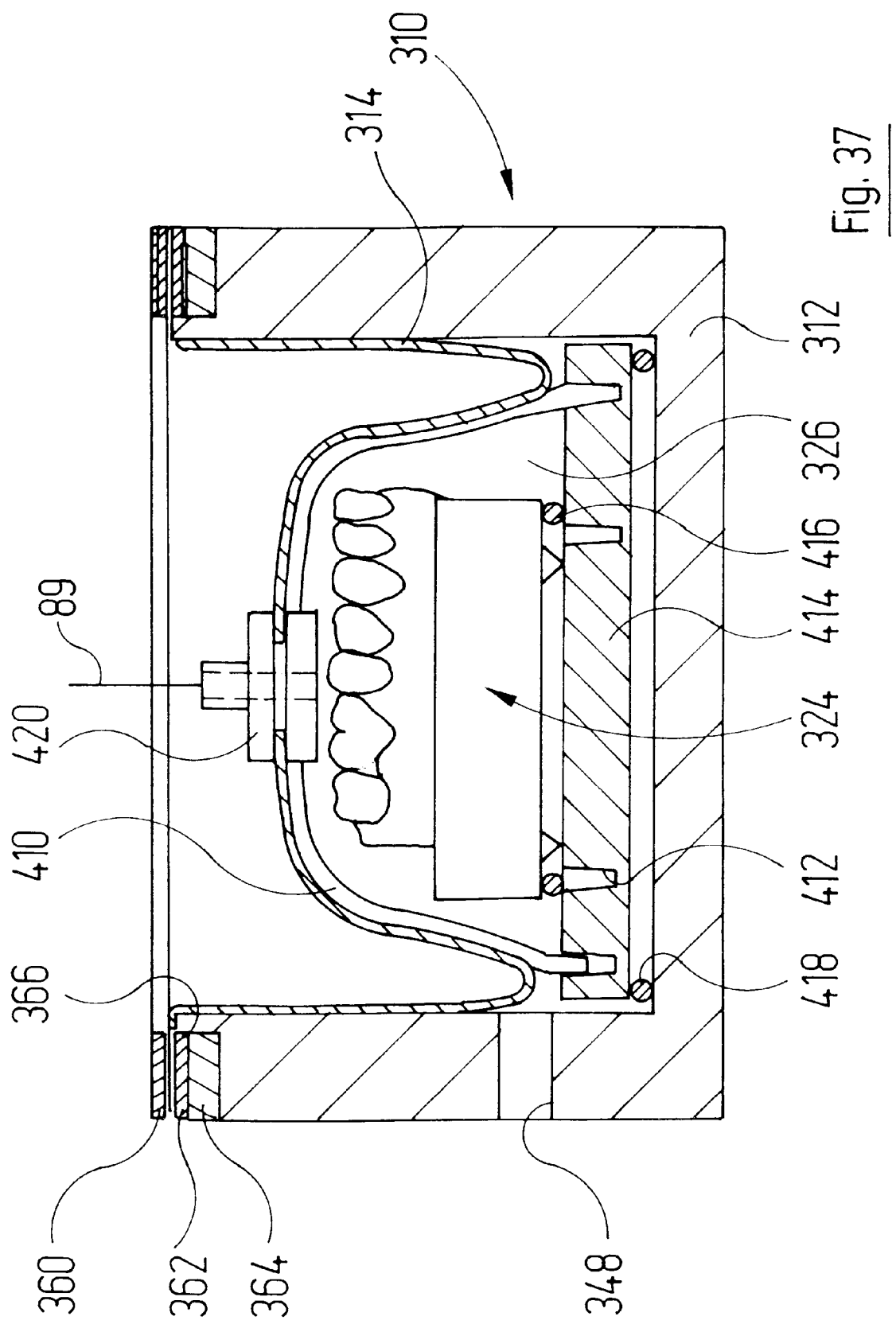

The copying device shown in FIG. 37 operates in a similar way to that according to FIG. 35, the difference being that the supporting body 390 is arranged under the impression space membrane 314 and remains as a reinforcement in the model impression. The supporting body according to FIG. 37 comprises a plurality of supporting straps 410 whose ends are fastened in conical bores 412 of a base plate 414.

A peripheral seal 416 is provided between the underneath of the tooth model 324 and the upper side of the base plate 414. A further seal 418 lies between the lower edge of the base plate 414 and the floor of the housing 312.

The base plate 414 may also be dispensed with and the floor of the copying device itself may be appropriately shaped.

The impression space membrane 314 is secured to the housing 312 in a similar way to that described above with reference to FIG. 31.

A plurality of angularly displaced feed openings 348 are provided in the housing 312 for the addition of the impression material. For the vacuum charging of the impression space 326 a fitting 420 is tightly inserted into the middle of the impression space membrane 314. On applying a reduced pressure the impression space membrane is urged tightly against the supporting framework formed by the supporting straps 410.

A locking element (not shown) is inserted into the end of a vacuum connection line 89 communicating with the fitting 420, the locking element being blocked by impression material so that the latter cannot reach the suction unit. The locking element may for example be a cotton wool plug.

In the copying device shown in FIG. 37 the shape which the impression space membrane 314 adopts under operating conditions can be predetermined by suitably bending and altering the length of the individual supporting straps 410. It is understood that the straps are installed with small interspacings so as to avoid impermissibly large saggings in the impression space membrane, and if necessary not only mutually parallel supporting straps but also transverse supporting straps may be provided.

In the aforedescribed impression process the impression cavity was in each case defined by a tray and the surface of which an impression was to be made and neighbouring elastically flexible materials (soft tissue or elastic sealing wall). In this connection the objective was to keep the impression space as small as possible in order to save impression material.

It is understood that in regions in which the tray or the impression space membrane cannot be brought close to the surface of which an impression is to be made, dead space bodies may in addition be used in order to save using expensive impression material to fill space regions that do not contain interesting details. Such dead space elements may for example be prefabricated standard elements that can be clipped off or stuck on at predetermined points on a tray or a model. It is understood however that these elements may also include plastically deformable elements that are introduced into regions of a tray or of the model corresponding to uninteresting regions of a model. Thus for example FIGS. 29 and 30 show a dead space body 422 that is formed by a kneading compound.

In a further developed embodiment of the invention that is not illustrated in the drawing, the cavity mould may also simply be a preferably plane parallel plate that is provided with a rigidly mounted rubber disc to provide a seal on a copying tray, which is designed for example according to FIGS. 32 or 34.

Instead of this a flexible seal may also be applied to the edge of the tray. Just as in the case of the production of intraoral partial impressions, models with position retaining parts may also be employed in the production of negative impressions if only partial copies are desired.

What is claimed is:

1. Device for producing tooth impressions, with a tray (1) that can cover a plurality of adjacent tooth positions of a jaw, the contour of the tray roughly matching the contour of the jaw, wherein the free edges of the tray walls (12, 16, 26) run so that they can form together with soft tissues of a patient's mouth a sealing point, and which is provided with at least one impression material connection element (30) communicating with the interior of the tray, and with a source (94 to 108) for liquid hardenable impression material (114) that is connected 148) to the impression material connection element (30), wherein the tray (1) has at least one vacuum connection element (32, 34, 36, 194, 198) communicating with the interior of the tray that is connected to a reduced pressure source (90, 92), wherein the reduced pressure source (90, 92) produces a pressure drop in the range between 10 and 500 mbar.

2. Device as claimed in claim 1, wherein the reduced pressure source (90, 92) establishes a pressure drop between 10 and 200 mbar.

3. Device as claimed in claim 2, wherein the reduced pressure source has a suction arrangement (92) and a reduced pressure regulator (90) connected in front of its suction opening.

4. Device as claimed in claim 3, wherein the suction arrangement has a venturi nozzle (162) whose feed inlet is connected to a compressed air line (164).

5. Device as claimed in claim 2, wherein the pressure drop in between 50 and 150 mbar.

6. Device as claimed in claim 1, wherein an impression material distributor tube (28) extends in the longitudinal direction of a curved impression space (52) predetermined by the tray (1), which tube has at least one opening, and preferably also has at least one outlet opening (140) in the tube wall, open to the interior of the tray, an outlet opening pointing to the tooth position.

7. Device as claimed in claim 6, in which the tray (1) covers a whole tooth arch and has a symmetrical shape relative to a longitudinal centre plane, wherein the distributor tube (28) is likewise symmetrical relative to the longitudinal centre plane of the tray and is extended by the two arms of the impression space (52) having a U-shaped geometry in plan view.

8. Device as claimed in claim 6, wherein an outlet opening pointing to the tooth position is provided for each tooth position.

9. Device as claimed in claim 1, wherein the tray (1) has a plurality of vacuum connection elements (32, 34, 36, 194, 198), which are arranged symmetrically to its longitudinal centre plane.

10. Device as claimed in claim 9, wherein at least some of the vacuum connection elements (32, 34, 36, 194, 198) communicate with associated vacuum distributor lines (186), which extend over a plurality of teeth positions and have at least one suction opening 190.

11. Device as claimed in claim 10, wherein the tube walls of the vacuum distributor lines (186) have a plurality of outlet openings (190) spaced apart in the longitudinal direction, which differ at least in some cases in their diameter and/or their alignment.

12. Device as claimed in claim 10, wherein the vacuum distribution lines have a suction opening for each of the teeth positions.

13. Device as claimed in claim 9, wherein the vacuum connection elements (32, 34, 36, 194, 198) are connected via a common reduced pressure line (89) to the reduced pressure source (90, 92).

14. Device as claimed in claim 9, wherein the vacuum connection elements are arranged symmetrically to the longitudinal center plane of the tray.

15. Device as claimed in claim 1, wherein the impression material connection elements (30) and the vacuum connection elements (32, 34, 36, 194, 198) are carried by a tray section (4, 118) formed as a disposable part, whereas the reusable remainder of the tray is formed as a sterilizable part.

16. Device as claimed in claim 15, wherein the disposable tray part (118) has at least one material longitudinal web (138) running in the longitudinal direction of the impression space (52) and a plurality of transverse webs (136) running between the latter web and the external edge wall (120) of the disposable tray part (118), the material longitudinal webs (138) and the transverse webs (136) being designed so that they permit a flow of the impression material in the longitudinal direction of the dental arch and/or in a direction perpendicular thereto.

17. Device as claimed in claim 15, wherein the impression material distributor tube (28) is connected to the tray edge part (118).

18. Device as claimed in claim 17, wherein the distribution tube is embedded wholly or partly in the tray edge part.

19. Device as claimed in claim 1, wherein the impression material connection elements (30) and the vacuum connection elements (32, 34, 36, 194, 198) are carried by a central section (146) of an external edge wall (16) of the tray (1), the central section (146) of the external edge wall (16), being formed as a handle.

20. Device as claimed in claim 19, wherein the impression material connection element (30) is arranged in an apron (146) of the external edge wall (120) of a disposable tray part (118), which element engages in a complementary recess (147) of the external edge wall (16) of a reused tray part (116).

21. Device as claimed in claim 19, wherein the vacuum connection elements are carried by a central section of an external edge wall of the tray in combination with the connection elements.

22. Device as claimed in claim 19, wherein the central section is formed as a handle.

23. Device as claimed in claim 15, wherein the cooperating edges of the reused tray part (116) and disposable tray part (118) are sealed with respect to one another via a groove/tongue joint (122, 124) and/or a seal (130, 132).

24. Device as claimed in claim 1, wherein the free edge of the tray (1) carries an elastically flexible seal (70, 78, 176, 178).

25. Device as claimed in claim 24, wherein the seal (176) is carried by a bendable section (174) of a disposable tray part (118).

26. Device as claimed in claim 24, wherein the seal (178) is an expandable flexible hollow body that is connected to a compressed air source (182), or is an elastically deformable hollow body.

27. Device as claimed in claim 1, wherein the tray (1) is wholly or partly made of transparent material, and in addition the vacuum connection elements (32, 34, 36) are also made of transparent material, in particular transparent plastics material.

28. Device as claimed in claim 27, wherein the transparent material comprises plastic material.

29. Device as claimed in claim 27, wherein the vacuum connection elements are made of transparent material.

30. Device as claimed in claim 27, wherein the vacuum connection elements are made of transparent plastic material.

31. Device as claimed in claim 1, wherein a section of the interior of the tray (1) is separated by a sealing wall (150) from the impression space (52), the free edge of the sealing wall (150) being able to be placed tightly against the intraoral soft tissue, and that a separate suction line (154) leads to the suction space (152) bounded by the sealing wall (150), which suction line is connected to a separate vacuum connection piece (156) that in turn is connected to a reduced pressure source, (90, 92) communicating with the impression space (52).

32. Device as claimed in claim 31, wherein the reduced pressure source communicates with the impression space.

33. Device as claimed in claim 1, wherein the passage cross-section of the connection elements (30) for the impression material corresponds to the area of a circle having a diameter of about 2 to 8 mm.

34. Device as claimed in claim 33, wherein the circle has a diameter of about 4 to 6 mm.

35. Device as claimed in claim 1, wherein the impression material source (94 to 108) provides the impression material under excess pressure.

36. Device as claimed in claim 35, wherein the excess pressure is adjustable.

37. Device as claimed in claim 1, wherein there is a rinse fluid source (170) that can be connected to the impression material connection element (30).

38. Device as claimed in claim 37, wherein the rinse fluid source (170) provides a fluid containing at least one active constituent 39. Device as claimed in claim 1, wherein an impression material locking element (156, 158, 160) is arranged at or in the vacuum connection elements (32, 34, 36).

40. Device as claimed in claim 39, wherein the impression material locking element (156, 158, 160) contains a filter element.

41. Device as claimed in claim 39, wherein the impression material locking element contains additional hardener material and/or additional catalyst material.

42. Device as claimed in claim 1, wherein the impression material connection element (30) has a closure means.

43. Device as claimed in claim 42, wherein the closure means is a valve (110) or a sealing foil that is forcibly opened when the source (94 to 108) for the liquid hardenable impression material (114) is connected to the impression material connection element (30).

44. Device as claimed in one of claims 7 to 43, wherein the tube wall of the impression material distributor tube (28) has a plurality of outlet openings (140) spaced apart in the longitudinal direction, which differ at least in some cases in their diameter and/or their alignment.

45. Impression tray for use in a device as claimed in claim 1, wherein it has a tray base part (210) and a distributor part (212) mounted on its external wall (214), that the tray base part (210) has in its external wall at least one impression material feed opening (232) and/or at least one vacuum feed opening (234, 236) spaced therefrom, and that an impression material feed channel arrangement (250, 251, 252) is provided in the distributor part (212), which arrangement connects the impression material connection element (240) carried by the distributor part (212) to the impression material feed openings (232), and/or a vacuum feed channel arrangement (248) is provided, by means of which at least one vacuum connection element (242, 244) carried by the distributor part (212) is connected to the vacuum feed openings (234, 236).

46. Impression tray as claimed in claim 1, wherein the tray base part (210) and/or the distributor part (212) is a plastics moulding.

47. Impression tray as claimed in claim 1, wherein the tray base part and/or the distributor part (212) is a metal moulding.

48. Impression tray as claimed in claim 1, wherein the various connection elements (240, 242, 244, 246) are arranged closely adjacent in the anterior end section of the distributor part (212).

49. Impression tray as claimed in claim 1, wherein the vacuum feed channel arrangement (248) has, looking in the flow direction, at least one impression material lock (249) in front of at least one vacuum feed opening (236).

50. Impression tray as claimed in claim 49, wherein the impression material locks (249) are in each case formed by a raised section of the floor of a distributor groove (248), which is part of the vacuum feed channel arrangement.

51. Device as claimed in claim 1, wherein the tray (210, 212) has a feed opening (232) communicating with a first end of the impression space and a second feed opening (234) communicating with a second end of the impression space.

52. Device as claimed in claim 51, wherein the tray (328) has an external circumferential wall (332–336) that is adjustable as regards height.

53. Device as claimed in claim 52, wherein the circumferential wall has a stationary wall part (332) and a vertically movable wall part (336) in a groove (334) of the latter, as well as means (340) for predetermining the spacing between the movable wall part (336) and stationary wall part (332).

54. Device as claimed in claim 53, wherein the movable wall part (336) is pretensioned in an extended position by means of a spring arrangement (342).

55. Device as claimed in claim 51, wherein at least one of the feed openings (348, 350) is provided in an, under operating conditions, rear wall (352) of the tray (328).

56. Impression tray as claimed in claim 1, wherein at least one vacuum feed opening (236) is provided in the anterior end section of the tray base part (210).

57. Impression tray as claimed in claim 1, wherein at least one impression material feed opening (232) is arranged in a distal end section of the tray base part (210).

58. Impression tray as claimed in claim 1, wherein the sections of the channel arrangements of the distributor part (212) adjacent to the feed openings (232, 234, 236) are formed as open grooves (248, 252) up to the tray base part (10).

59. Impression tray as claimed in claim 1, wherein the tray base part (210) and the distributor part (212) have cooperating positioning means (228, 230).

60. Impression tray as claimed in claim 59, wherein the positioning means have positioning grooves (228) and positioning ribs (230), which extend in the vicinity of the edges of the external wall (214) of the tray base part (210).

61. Impression tray as claimed in claim 1, wherein the distributor part (212) is detachably connected by means of an catch connection (238) to the tray base part (210).

62. Impression tray as claimed in claim 1, wherein the boundary surface of the distributor part (212) facing the tray base part (210) has at least one suction pocket (258) that is connected via a further channel arrangement (254, 256) of the distributor part (212) to a separate vacuum connection element (246).

63. Impression tray as claimed in claim 1, wherein at least one section (226) of the tray base part (210) is made of transparent material.

64. Impression tray as claimed in claim 1, wherein the feed openings (232, 234, 236) and the channel arrangements (248, 250, 251, 252, 254, 256) are symmetrical relative to a longitudinal centre plane of the impression tray.

65. Impression tray as claimed in claim 64, wherein two vacuum connection elements (242, 244) are provided in the anterior end section of the distributor part (212), which elements communicate via a section of the vacuum feed channel arrangement (248) with a central vacuum feed opening (236).

66. Impression tray as claimed in claim 65, wherein the elements communicate with two lateral vacuum feed openings approximately at the height of the canine tooth position of the tray base part.

67. Device as claimed in claim 1, wherein the tray (1) has a bowl-shaped rigid tray housing (330, 332) and an elastically deformable impression space membrane (314) secured to the latter.

68. Device as claimed in claim 67, wherein there are means (390, 89) for contouring the impression space membrane (314).

69. Device as claimed in claim 68, wherein the contouring means have a contoured supporting element (390) and means (89) for pretensioning the impression space membrane (314) against the supporting element (390).

70. Device as claimed in claim 69, wherein the supporting element (390, 392) is lattice-like or open-pore and the pretensioning means have a reduced pressure source that can be connected to the working space (386) bounded by the impression space membrane (314) and the tray housing.

71. Device as claimed in claim 69, wherein the pretensioning means have a pressure source that can be connected to the impression space (326) in front of the impression space membrane (314).

72. Impression tray as claimed in claim 1, wherein the external surface (260) of the distributor part (212) is spherical.

73. Device as claimed in claim 1, wherein there is a cavity mould (310) on which an object (324) of which an impression is to be made can be secured (320, 322), and which has a deformable sealing wall (314) surrounding the object (324) of which an impression is to be made, which together with the tray (328) defines a sealed impression space (326).

74. Device as claimed in claim 73, wherein the sealing wall comprises elastically deformable material (374).

75. Device as claimed in claim 74, wherein the free front surface of the foam material has a tight surface skin (376) or carries a film impermeable to flow media.

76. Device as claimed in claim 73, wherein the tray (328) has an impression space membrane (314) running over the model (324) and means (392, 394–400) are provided for subjecting different regions of the impression space membrane (314) to different loads, the impression space membrane (314) being secured to a lower section of a housing (312) of the cavity mould (310).

77. Device as claimed in claim 76, wherein the loading means have weights (394–440) adapted to different regions of the model (324).

78. Device as claimed in claim 77, wherein it has at least one position indicator (402–408) cooperating with one of the weights (394–400).

79. Device as claimed in claim 76, wherein the impression space membrane is secured to a lower section of a housing of the cavity mould.

80. Device as claimed in claim 73, wherein the sealing wall (314) has a sealing membrane secured on a housing (312) of the cavity mould (310).

81. Device as claimed in claim 80, wherein the sealing membrane (314) together with the housing (312) defines a membrane rear space (358) that is filled with a fluid (372).

82. Device as claimed in claim 81, wherein the fluid is a gas under reduced pressure, whereby the sealing membrane (314) is prestressed into a concave shape.

83. Device as claimed in claim 81, wherein the fluid is a liquid or a gel.

84. Device as claimed in claim 51, wherein there is a pressure regulator (368) communicating with the membrane rear space (358).

85. Device as claimed in claim 53, wherein the movable wall part (336) is sealed by a sealing arrangement (338) against the groove (334) of the stationary wall part (332).

86. Device as claimed in claim 1, wherein the tray (328) is a one-pieced disposable part made of plastics material, in particular a deep-drawn part.

87. Device as claimed in claim 86, wherein the disposable part comprises a deep-drawn disposable part.

88. Device as claimed in claim 1, wherein at least one feed opening (346) of the tray (328) that can be connected to a vacuum source is arranged in an, under operating conditions, upper wall section (330) of the tray.

89. Device as claimed in claim 1, wherein there is at least one dead space element (422) inserted in the tray (328), which is chosen from a plurality of standard dead space elements or is plastically deformable.

90. A process for producing tooth impressions with a tray that covers a plurality of adjacent tooth positions, the contour of the tray roughly matching the contour of a jaw, an impression space (52) being predetermined by the tray, the free edges of the tray forming a sealing place with the soft tissue of a patient's mouth, the tray having at least one impression material connection element communicating with the interior of the tray, comprising connecting an impression material source containing a hardening catalyst (94 to 108) to the impression material connection, selecting and metering the catalyst and adjusting a reduced pressure in the impression space (52) and a discharge pressure of the impression material source (94 to 108) relative to one another so that hardening of the impression material takes place only after the impression space (52) has been completely filled.

* * * * *